United States Patent
Leung et al.

(10) Patent No.: US 11,040,015 B2
(45) Date of Patent: Jun. 22, 2021

(54) METHOD OF LONG-TERM PRESERVATION OF CHEMICAL AND BIOLOGICAL SPECIES USING SUGAR GLASSES

(71) Applicant: McMaster University, Hamilton (CA)

(72) Inventors: Vincent Ho Yin Leung, Mississauga (CA); Sana Jahanshahi-Anbuhi, Hamilton (CA); Carlos Filipe, Ancaster (CA); M. Monsur Ali, Hamilton (CA)

(73) Assignee: McMaster University, Hamilton (CA)

( * ) Notice: Subject to any disclaimer, the term of this patent is extended or adjusted under 35 U.S.C. 154(b) by 70 days.

(21) Appl. No.: 16/161,627

(22) Filed: Oct. 16, 2018

(65) Prior Publication Data

US 2019/0111006 A1    Apr. 18, 2019

Related U.S. Application Data

(60) Provisional application No. 62/572,928, filed on Oct. 16, 2017.

(51) Int. Cl.

| | |
|---|---|
| *A61K 39/39* | (2006.01) |
| *A61K 39/42* | (2006.01) |
| *A61K 47/26* | (2006.01) |
| *A61K 47/28* | (2006.01) |
| *A61K 9/28* | (2006.01) |
| *A61K 9/70* | (2006.01) |
| *A61K 9/48* | (2006.01) |
| *A61K 39/12* | (2006.01) |
| *A61K 9/00* | (2006.01) |
| *A61K 47/36* | (2006.01) |
| *A61K 39/00* | (2006.01) |

(52) U.S. Cl.
CPC .......... *A61K 9/7007* (2013.01); *A61K 9/0034* (2013.01); *A61K 9/286* (2013.01); *A61K 9/2826* (2013.01); *A61K 9/4816* (2013.01); *A61K 9/4833* (2013.01); *A61K 39/12* (2013.01); *A61K 39/39* (2013.01); *A61K 39/42* (2013.01); *A61K 47/26* (2013.01); *A61K 47/28* (2013.01); *A61K 47/36* (2013.01); *A61K 9/006* (2013.01); *A61K 2039/5254* (2013.01); *A61K 2039/6093* (2013.01); *C12N 2710/16634* (2013.01); *C12N 2710/16651* (2013.01); *C12N 2760/16134* (2013.01); *C12N 2760/16151* (2013.01); *C12N 2795/10151* (2013.01)

(58) Field of Classification Search
CPC .. A61K 9/7007; A61K 9/2826; A61K 9/0034; A61K 9/286; A61K 9/4833; A61K 9/4816; A61K 39/12; A61K 39/39; A61K 39/42; A61K 47/26; A61K 47/28; A61K 47/36

See application file for complete search history.

(56) References Cited

U.S. PATENT DOCUMENTS

| | | |
|---|---|---|
| 7,749,538 B2 | 7/2010 | Sugimoto et al. |
| 9,974,850 B2 | 5/2018 | Croyle et al. |

FOREIGN PATENT DOCUMENTS

| | | | |
|---|---|---|---|
| WO | 00/50013 | * | 8/2000 |

OTHER PUBLICATIONS

Stankovic (Chemical and Technical Assessment 65th JECFA, Chemical and Technical Assessment for Pullulan, pp. 1-8, accessed Jun. 19, 2020 from http://www.fao.org/fileadmin/templates/agns/pdf/jecfa/cta/65/pullulan.pdf) (Year: 2020).*
Merabishvili, M. et al., Stability of *Staphylococcus aureus* Phage ISP After Freeze-Drying (Lyophilization), PLoS ONE, vol. 8(7), Jul. 2, 2013, pp. 1-7.
Leung, V. et al. Long-Term Preservation of Bacteriophage Antimicrobials Using Sugar Glasses. ACS Biomater. Sci. Eng. (2018) 4, 11, 3802-3808, published online Oct. 16, 2017.
Leung, V. et al., Ready-to-use thermally stable mastermix pills for molecular biology applications, Biotechnology Progress, American Chemical Society (ACS), 2019, vol. 35(2), e2764; epublished Dec. 24, 2018.
Leung, V. et al., Long-Term Antimicrobial Activity of Phage—Sugar Glasses is Closely Tied to the Processing Conditions, ACS Omega, American Chemical Society, vol. 3(12), 2018, pp. 18295-18303.
Leung, V. et al., Thermal Stabilization of Viral Vaccines in Low-Cost Sugar Films, Nature, May 21, 2019, 9:7631.
Leung, V. et al., Long-Term Preservation of Bacteriophage Antimicrobials Using Sugar Glasses, Biomaterials, Science & Engineering, 2018, 4:3802-3808.

* cited by examiner

*Primary Examiner* — Alma Pipic
(74) *Attorney, Agent, or Firm* — Bereskin & Parr LLP/S.E.N.C.R.L., s.r.l.; Patricia Folkins

(57) ABSTRACT

A method of preserving the one or more chemical and/or biological species in a polymer matrix comprising pullulan and trehalose is described. The method includes combining the one or more chemical and/or biological species, an aqueous pullulan and a trehalose solution and drying the resultant mixture to provide a solid polymeric matrix. A polymeric matrix comprising one or more chemical and/or biological species and its use, for example, on surfaces for food preparation, for food preservation and in biological preparations is also described.

23 Claims, 13 Drawing Sheets

Figure 9

METHOD OF LONG-TERM PRESERVATION OF CHEMICAL AND BIOLOGICAL SPECIES USING SUGAR GLASSES

RELATED APPLICATIONS

The present application claims the benefit of priority of U.S. provisional patent application No. 62/572,928, filed on Oct. 16, 2017, the contents of which are incorporated herein by reference in their entirety.

FIELD

The present application relates to the preservation and/or stabilization of chemical and/or biological species in sugar glasses, in particular materials comprising pullulan and trehalose. The application includes the materials and methods for their use in stabilizing and/or preserving chemical and/or biological species.

BACKGROUND

Bacteriophages (phages) are viruses that infect bacteria. From the early days of their discovery in 1917, lytic bacteriophages have been used as potent antimicrobial agents.[1,2] An advantage of phage over other antimicrobial agents is its specificity. Whereas most broad-spectrum antimicrobial agents function like a sledgehammer, wiping out any and all bacteria, bacteriophages specifically target only certain species/strains of bacteria within a mixed population. This specificity has made bacteriophage antimicrobials very attractive for food processing/packaging applications, amongst others.[3-11] The odor, taste, and texture of most food products, particularly fresh produce, is negatively affected by commercial antimicrobial agents. Bacteriophages exist naturally on fruits and vegetables and adding phage antimicrobials will not affect the appearance, taste, odor, or texture of produce.[12] Bacteriophage antimicrobials are also particularly useful for decontaminating products such as cheese for which the quality of the product strongly depends on the presence of beneficial bacteria, or honey which is consumed raw and without additives or antibiotics. In addition to their specificity, phage antimicrobials have garnered significant attention in the past 20 years as a result of the ever-growing crisis of antibiotic resistance.[13-16] Presence of multidrug resistant bacteria in animal products poses a serious threat to public health, especially in countries where antibiotics are used liberally and without constraint as an integral part of animal husbandry.[17,18]

Using phage-impregnated coatings on food preparation surfaces, surfaces in food processing plants, and for food packaging may be a promising way to ensure food safety.[5,8,14,19] However, to effectively incorporate phage as part of a functional antimicrobial coating, certain challenges must be addressed, including the issue of phage stability.[7] Bacteriophages are generally resilient to most environmental conditions such as temperature, pH, and salt concentration, although their sensitivity varies significantly amongst strains.[20] However, desiccation cannot be endured by many phages and thus a challenge in developing phage-functionalized coatings is finding methods to protect phage against the effects of desiccation.

Amongst methods proposed to date for long-term stabilization of bacteriophage preparations, freeze-drying[21,22] (also known as lyophilization) and freezing in liquid nitrogen are the most prevalent. Neither method can preserve phage stability unless a protectant, such as glycerol, alginate,[8,23-28] pectin,[24,29] chitosan,[25,26] whey protein,[16,30] liposome,[31,32] poly(ethylene oxide)/cellulose diacetate,[33] and sucrose/trehalose[34] is present. Also, the lyophilized samples must be maintained in vacuum ampoules for effective phage stabilization. Both methods require access to specialized equipment for sample preparation (freeze dryer, vacuum pumps) and sample storage (liquid nitrogen storage).

Vaccines are an essential part of global health. Every year, millions of lives are saved through vaccination. Unfortunately, almost all available vaccines are thermally labile and must be kept between 2-8° C. at all times to retain their efficacy.[35] Failure to maintain an uninterrupted refrigerated supply chain from production to dispensation, called the "cold chain," leads to vaccine wastage and administration of ineffective vaccines.[36] The need for refrigeration is one of the major causes of under-vaccination globally as the cold chain presents economical and logistical problems for vaccination programs. The problem is especially serious for developing countries and remote areas where there are often a lack of dependable cold chain infrastructure and access to reliable electricity is limited.[37-39]

The development of thermally-stable vaccines that can remain active outside of the cold chain can greatly increase the accessibility of vaccination programs and significantly decrease the cost. Therefore, significant efforts have been made in creating thermally-stable vaccines and/or vaccine carriers. One approach has been to engineer vaccines that are thermally stable without preservative adjuvants. The engineering of protein-based vaccine had shown some promise.[40-43] Other reports modified viral vectors to create thermally stable viral vaccines.[44-45] Although designing thermally stable vaccines hold some promise, many of the engineered vaccine still have short shelf-life (~7 days) at elevated temperature (>37° C.). Moreover, engineering new vaccines is labor intensive and the new vaccines must obtain governmental approval before deployment.

Another common approach to thermally stabilize vaccine is the addition of stabilizing adjuvants[46] In addition to stabilizing adjuvants, vaccines are often dried to further increase thermal stability. Prausntz's group encapsulated inactivated influenza vaccine in microneedle patches with different stabilizing adjuvant formulations and the vaccine maintained immunogenicity after 4 months at 60° C.[47-49] Lyophilized anthrax vaccine was found to have preserved immunogenicity after 16 weeks at 40° C.[50] and lyophilized recombinant ricin toxin A vaccine was stable after 4 weeks at 40° C.[51] Recombinant hepatitis B vaccine and a protein-polysacharide conjugate vaccine for meningitis A was shown to be stable for 24 months at 37° C. after spray drying.[52] Foam drying of attenuated *Salmonella enterica* vaccine using trehalose methionine and gelatin were able to maintain vaccine potency for 12 weeks at 37° C.[53] Spray drying formulations using sugars and proteins with live attenuated measles vaccine were shown to be stable for up to 8 weeks at 37° C.[54] Lovalenti et al. stabilized live-attenuated influenza vaccines in a sucrose containing excipient using three drying methods, freeze drying, spray drying, and foam drying. It was found that foam drying with the right excipient composition produced the most thermally stable vaccine that had a shelf life of 4.5 months at 37° C.[55] Different lyophilized formulations of rotavirus vaccines were able to retain potency for 20 months at 37° C.[56] for up to 20 months.[57]. Alcock et al. used sucrose and trehalose to dry adenovirus and modified vaccinia virus Ankara onto polypropylene or glass fiber membranes, the viruses retained titer for up to 6 months at 45° C.[58] Many of the reports use freeze drying, spray drying, or foam drying which all require specialized equipment for sample preparation (freeze dryer, vacuum pumps) and expose vaccines to extreme temperatures or pressure conditions.[53] Moreover, some formulations require a large number of adjuvants which can increase the cost and complexity of the vaccine product.

Pullulan is a polysaccharide that has excellent film forming properties and has been used in the food industry as an oxygen barrier to prolong the shelf life of foods.[59-65] Previous studies have shown that pullulan is able to provide outstanding thermal stability and protection against oxidation of various labile biomolecules.[66-67] Trehalose is a disaccharide sugar that has been used extensively as a cryoprotectant and stabilizing agent during lyophilization.[68-79]

U.S. Pat. No. 7,749,538 describes a shaped product such as a film, sheet or film capsule shape having a high pullulan content in combination with trehalose wherein the content of the pullulan provides a shaped product that has stability to changes in humidity.

SUMMARY

The Applicants have found that the combination of pullulan and trehalose in a material, such as a film, coating or shaped object, creates a synergistic effect that leads to long-term stability of chemical and/or biological species, such as bacteriophages or virus, incorporated within the film.

Accordingly, the present application includes a polymer matrix comprising pullulan and trehalose and one or more chemical and/or biological species, wherein the one or more chemical and/or biological species are incorporated within the polymer matrix and the polymer matrix preserves and/or stabilizes the chemical or biological species.

The present application also includes a method of preserving and/or stabilizing one or more chemical and/or biological species comprising:
  a) combining the one or more chemical and/or biological species, an aqueous solution comprising pullulan and an aqueous solution comprising trehalose to provide a mixture; and
  b) drying the mixture to form a polymer matrix which preserves and/or stabilizes the one or more chemical and/or biological species.

The present application also includes a method of creating a film, coating or shaped object for preserving chemical or biological species comprising:
  a) combining one or more chemical or biological species with an aqueous pullulan and trehalose solution to provide the chemical or biological species in solution; and
  b) drying the solution to provide a solid polymeric film, coating or shaped object.

In some embodiments, at least one of the species is a biomolecule. In some embodiments, the biomolecule is selected from one or more of protein, enzyme, antibody, peptide, nucleic acid, phage, antidote and vaccine.

In some embodiments, at least one of the species a microorganism. In some embodiments, wherein the microorganism is selected from one or more of anaerobic bacteria, aerobic bacteria, mammalian cells, bacterial cells and viruses.

The present application also includes a pullulan/trehalose film, coating or shaped object comprising at least one or more chemical or biological species wherein the wt % pullulan in the dried pullulan/trehalose film, coating or shaped object is less than 50 wt %.

The present application also includes a dried pullulan/trehalose film, coating or shaped object comprising at least one or more chemical or biological species wherein the wt % pullulan in the dried pullulan/trehalose film, coating or shaped object is in the range of 30-45 wt %.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which:

Figure 9:
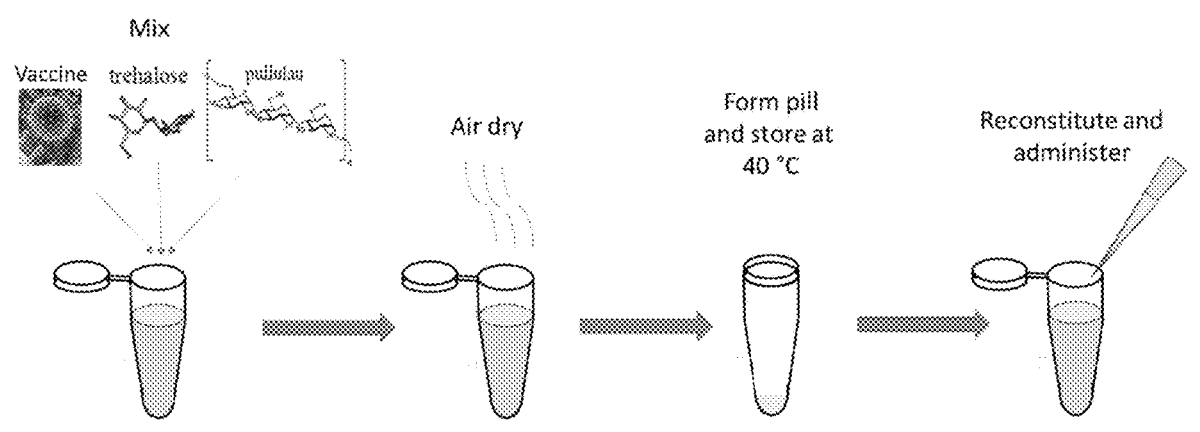

FIG. 9 shows the preparation, storage, and reconstitution of vaccines dried in exemplary pullulan and trehalose pills.

DETAILED DESCRIPTION

I. Definitions

Figure 1:
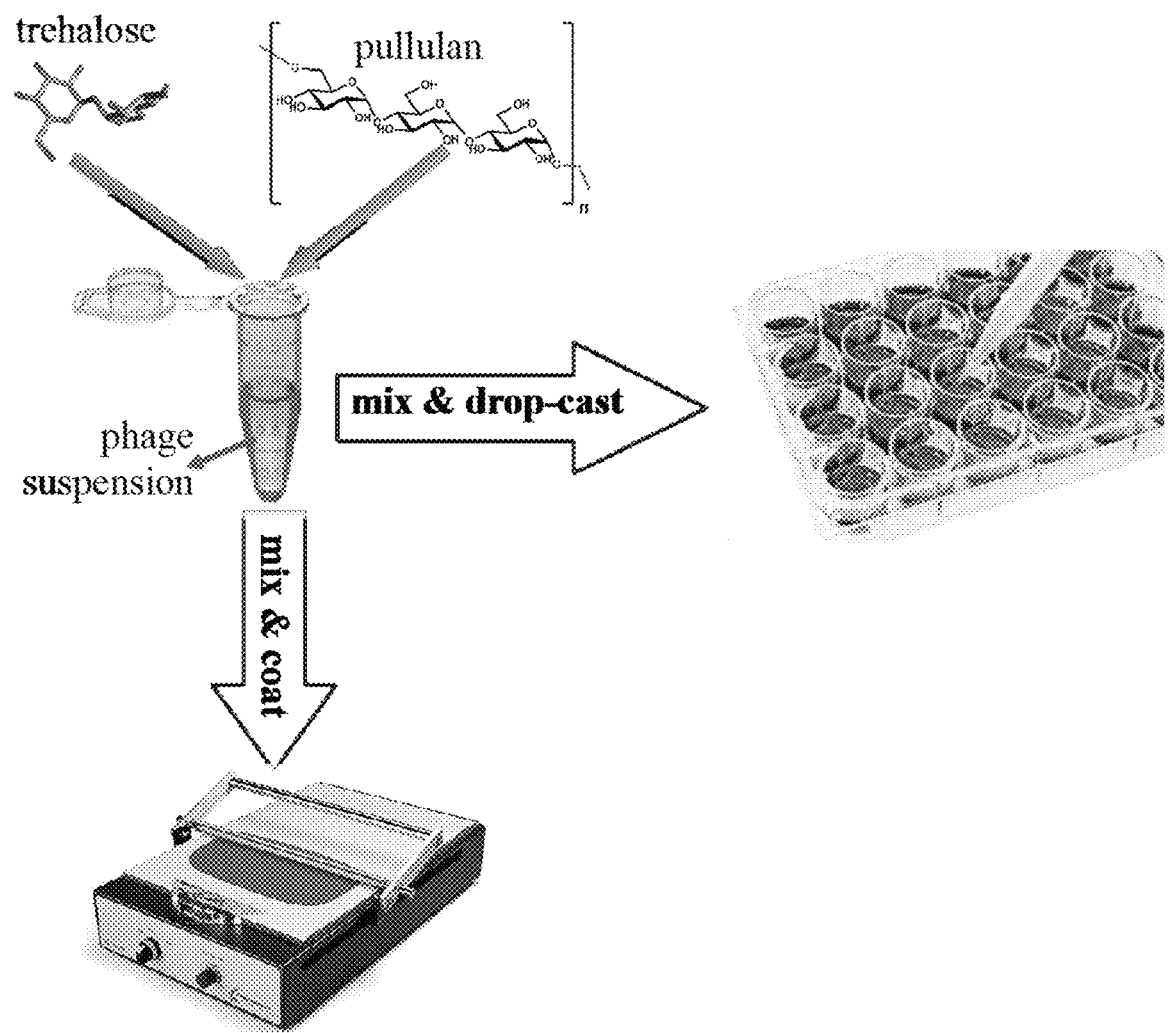
FIG. 1 shows a scheme demonstrating phage film formation and coating preparation in one embodiment of the application. The stabilizing films were prepared by mixing trehalose and pullulan with phage. The mixture was then either drop-cast (to form phage films) or coated on food packaging (to make antibacterial coatings).
Figure 2:
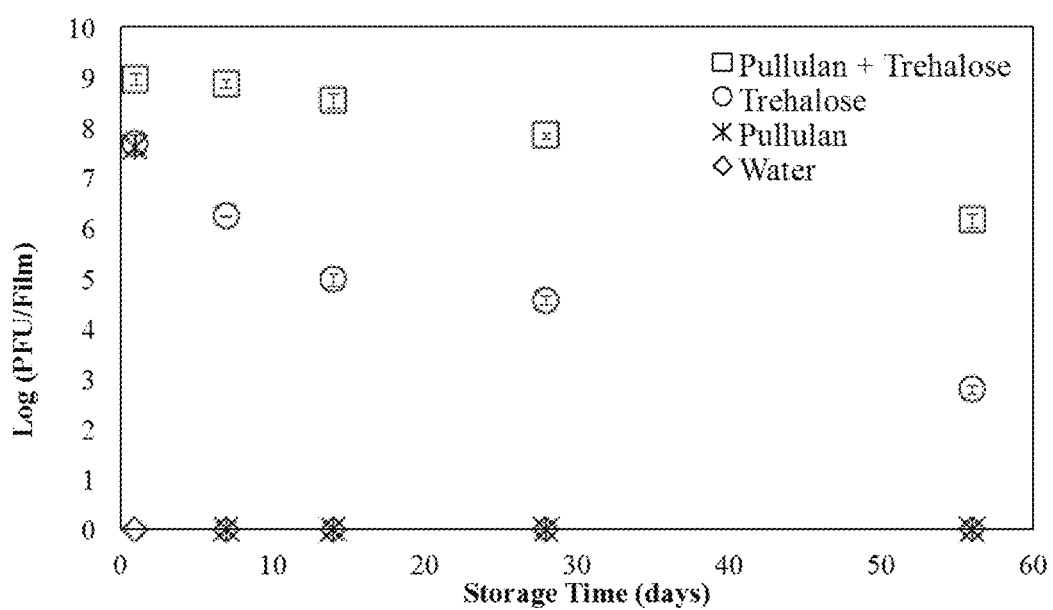
FIG. 2 shows the change in infectivity of dried LISTEX™ P100 with time when dried in different exemplary and comparative stabilizing matrixes as a function of storage time. The samples were stored in ambient conditions.
Figure 3:
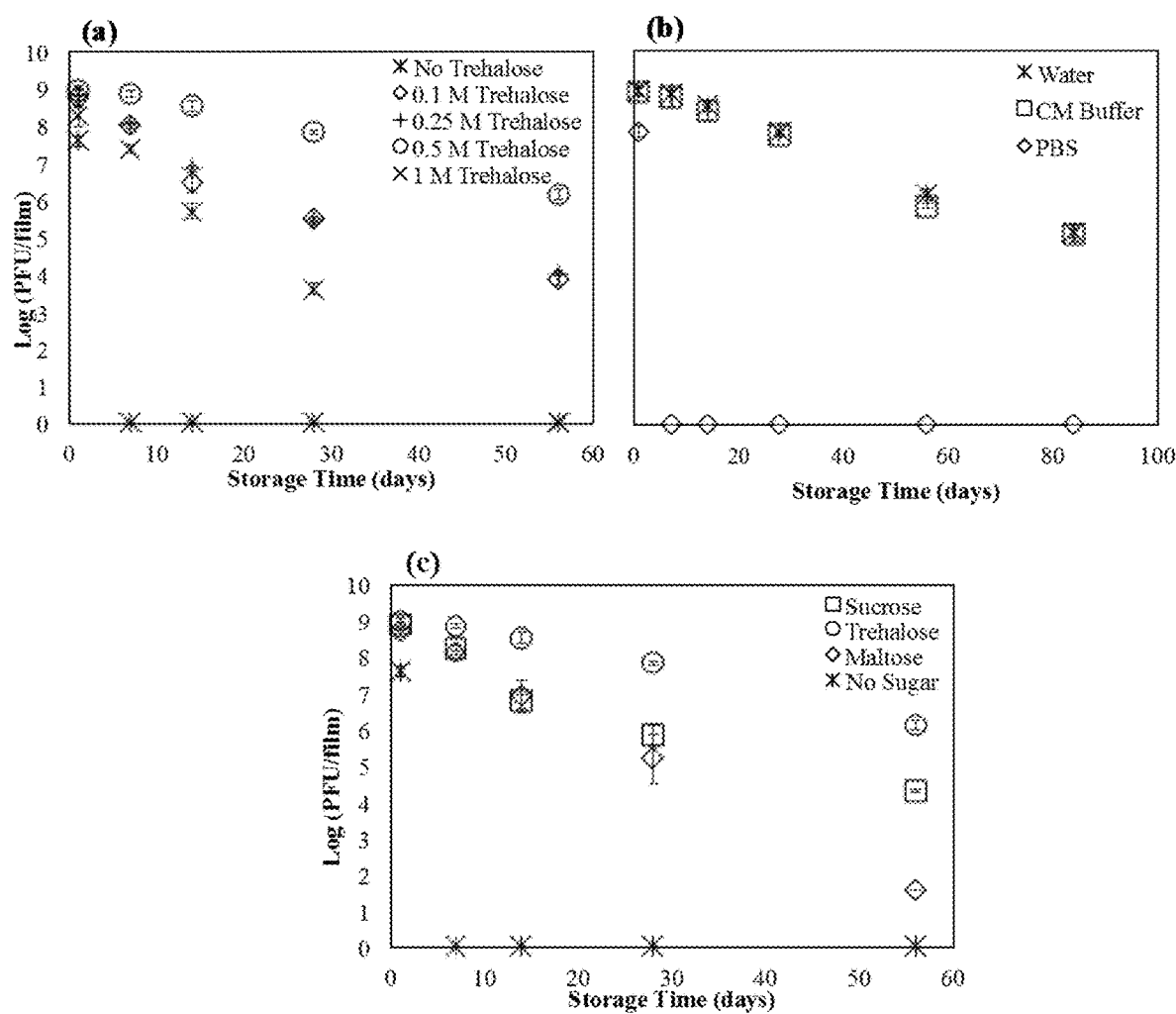
FIG. 3 shows a) the effect of trehalose concentration on the viability of LISTEX™ P100 in exemplary 10 wt % pullulan films as a function of storage time; b) the effect of casting buffers on the viability of LISTEX™ P100 in exemplary 10 wt % pullulan+0.5 M trehalose films as a function of storage time; and c) the effect of different disaccharides on phage stability as a function of storage time in 10 wt % pullulan. The concentration of each disaccharide used was 0.5 M. All samples were stored under ambient conditions.
Figure 4:
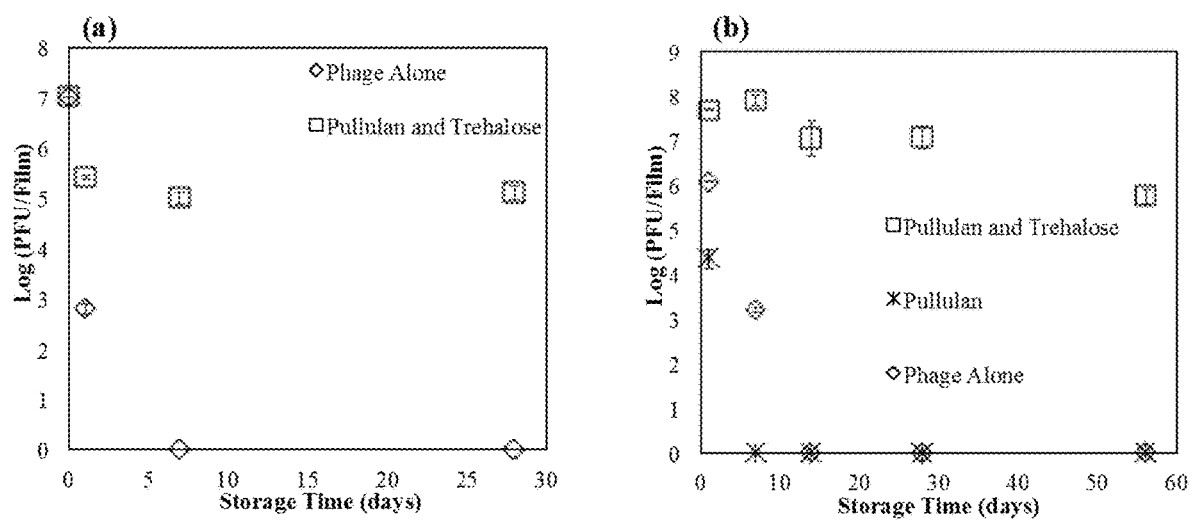
FIG. 4 shows a) infectivity of dried *E. coli* phage AG10 in exemplary pullulan-trehalose films compared with phage dried without pullulan and/or trehalose as a function of storage time and b) the infectivity of dried *Salmonella* phage CG4 in exemplary and comparative stabilizing matrixes as a function of storage time.
Figure 5:
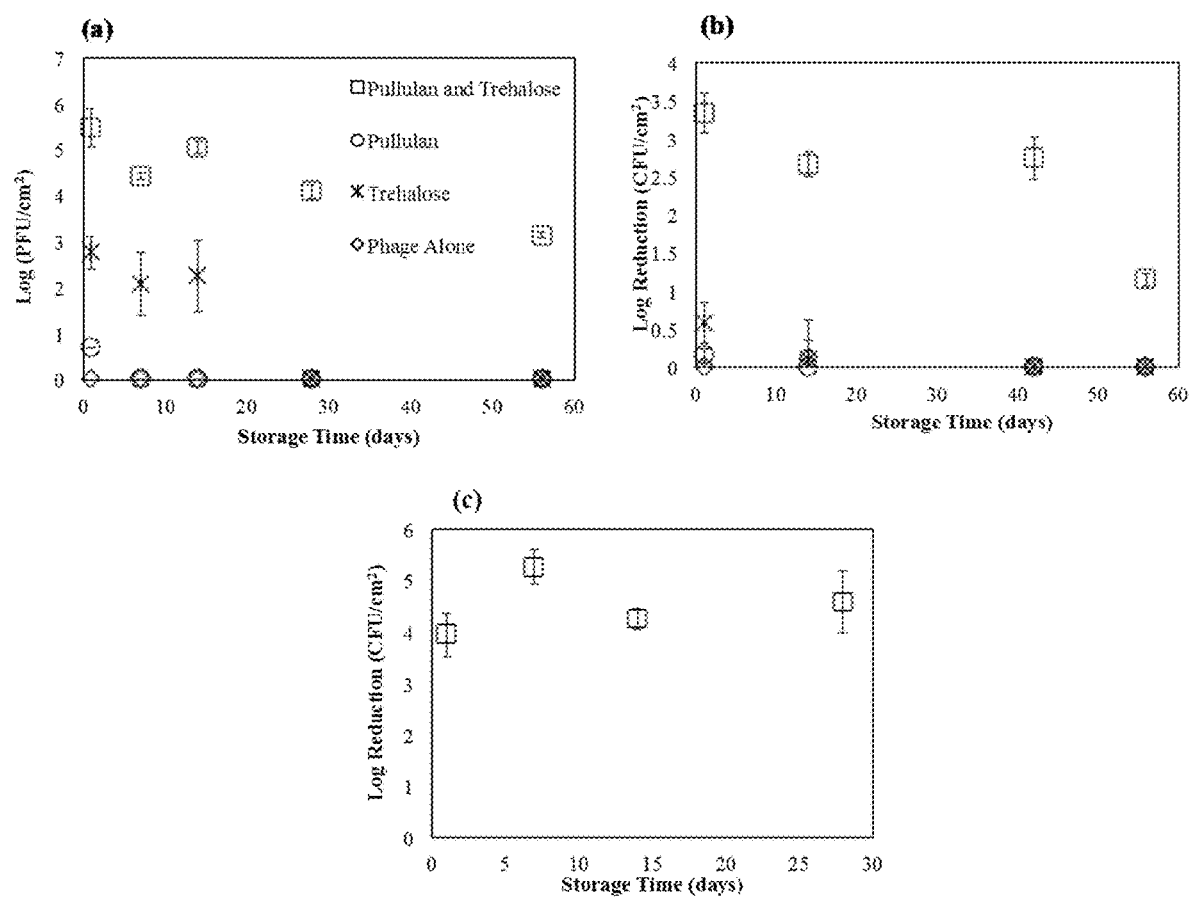
FIG. 5 shows a) the effect of different exemplary and comparative coating solutions on viable phage eluted from phage coated papers as a function of storage time; b) log reduction of colony forming units of *Listeria monocytogenes* by LISTEX™ coated paper using different exemplary and comparative coating solutions as a function of storage time; and c) log reduction of *Salmonella* Newport colony forming units as a function of storage time by CG4 phage coated paper using exemplary 10 wt % pullulan and 0.5 M trehalose. All samples were stored in ambient conditions
Figure 6:
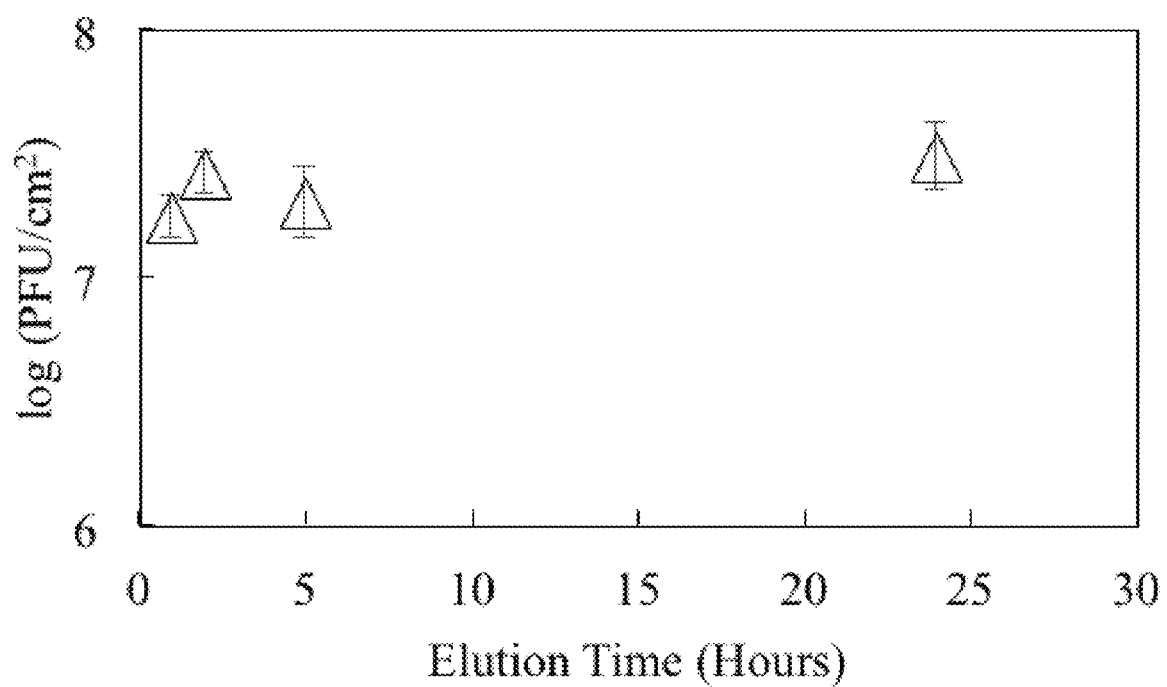
FIG. 6 shows phage eluted from untreated butcher paper at room temperature as a function of elution time.
Figure 7:
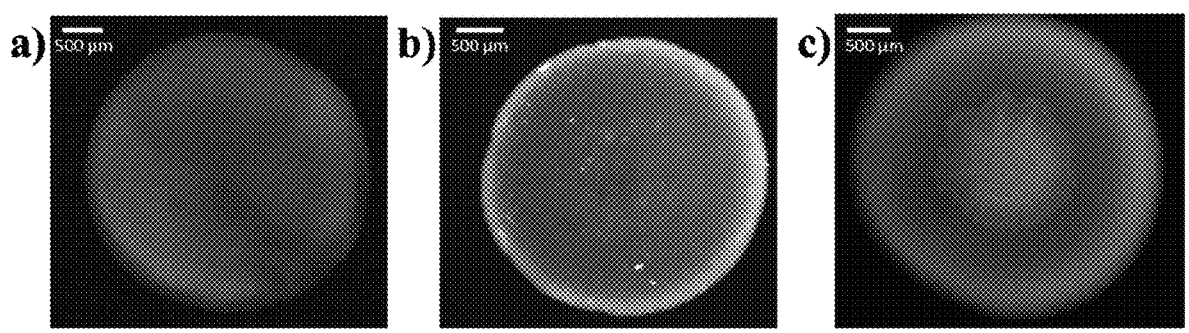
FIG. 7 shows microscope pictures of exemplary pullulan films casted in a) water; b) CM buffer; c) PBS.
Figure 8:
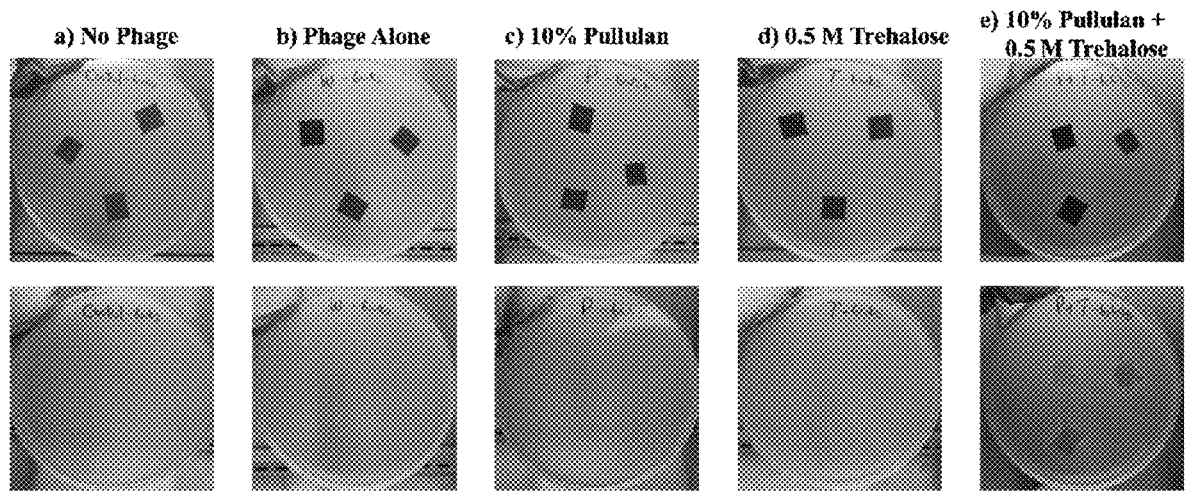
FIG. 8 shows the results of a plaque assay at 6 weeks storage time for phage-coated paper with different coating solutions: a) no phage; b) phage alone; c) 10 wt % pullulan and phage; d) 0.5 M trehalose and phage; e) exemplary 10 wt % pullulan, 0.5 M trehalose and phage

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a bacteriophage" or "a vaccine" should be understood to present certain aspects with one bacteriophage or vaccine, or two or more additional (and different) bacteriophage or vaccines.

The term "and/or" as used herein means that the listed items are present, or used, individually or in combination. In effect, this term means that "at least one of" or "one or more" of the listed items is used or present.

The term "biomolecule" as used herein means an organic macromolecule (such as a protein or nucleic acid) in living organisms.

The term "microorganism" as used herein means a microscopic organism that may exist as a single cell or as a colony of cells The term "preserving" or "preservation" as used herein with respect to the chemical and/or biological species means to maintain at least a measurable or detectable level of function or activity for the chemical and/or biological species for a desired period of time under specified conditions.

The term he term "stabilizing" or "stabilization" as used herein with respect to the chemical and/or biological species refers to any reduction in the degradation or loss of activity of the chemical and/or biological species compared to a control.

The term "drying" as used herein refers to a process of allowing a solution of a polymer to cure or set until a solid, movable material is obtained.

The term "pullulan" as used herein refers to a natural polysaccharide which is produced extracellularly by *Aurebasidium pullulans* when cultivated with starch hydrolyzates as a carbon source.

The term "trehalose" as used herein refers to (D)-(+)-trehalose which is a disaccharide composed of two glucose molecules bound together via the α,α-1,1-glucosidic linkage.

The expression "incorporated within" as used herein means that the one or more biological and/or chemical species are interspersed throughout the pullulan/trehalose polymer matrix.

The term "polymer matrix" as used herein means a material which is made of at least one polymer and which forms a surrounding medium or structure.

The term "food grade" as used herein means that the specified material is compatible for ingestion by humans and/or animals.

The term "medical grade" as used herein means that the specified material is compatible for administration to humans and/or animals.

II. Compounds and Compositions of the Application

The Applicants have found that a material made from pullulan and trehalose acts synergistically to provide a stabilized matrix that is capable of preserving and/or stabilizing chemical and/or biological species, such as bacteriophages and viruses, that are incorporated within the matrix.

Accordingly, the present application includes a polymer matrix comprising pullulan and trehalose and one or more chemical and/or biological species, wherein the one or more chemical and/or biological species are incorporated within the polymer matrix and the polymer matrix preserves and/or stabilizes the chemical or biological species.

In some embodiments the polymer matrix comprises about 10 wt % to about 50 wt % of pullulan and about 50 wt % to about 90 wt % of trehalose, based on the dry weight of the matrix. In some embodiments the polymer matrix comprises about 20 wt % to about 40 wt % of pullulan and about 60 wt % to about 80 wt % of trehalose, based on the dry weight of the matrix. In some embodiments the polymer matrix comprises about 30 wt % to about 45 wt % of pullulan and about 60 wt % to about 70 wt % of trehalose, based on the dry weight of the matrix. In some embodiments the polymer matrix comprises about 37 wt % of pullulan and about 63 wt % of trehalose, based on the dry weight of the matrix.

In some embodiments the pullulan has a molecular weight in the range of about 100,000 to about 200,000. Pullulan having such molecular weights is commercially available, for example from Hayashibara Co, Ltd., Okayama, Japan. Trehalose is available from a variety of commercial sources, including, for example, Hayashibara Co, Ltd., Okayama, Japan. In some embodiments, for use in food products, the pullulan and trehalose are both food grade materials. In some embodiments, for use in medical products, the pullulan and trehalose are both medical grade, or pharmaceutically acceptable, materials.

In some embodiments, the polymer matrix is formed into a dried film or a shaped object. In some embodiments, the dried film or shaped object is amorphous. In some embodiments, the film is a coating applied to a surface. In some embodiments, the film or coating, is applied to food, or is used as food packaging. In some embodiments, the film or coating is used as a wound dressing. In some embodiments, the film or coating is used in a filter, such as in a water filter. In some embodiments, the shaped object is a pill or capsule.

In some embodiments, the one or more chemical and/or biological species are preserved and/or stabilized without requiring refrigeration. In some embodiments, one or more chemical or biological species are preserved at a temperature of from about 2° C. to about 40° C., about 10° C. to about 30° C. or about 20° C. to about 25° C. In an embodiment, the one chemical or biological species are preserved and/or stabilized for at least 3 months at the above temperatures.

In some embodiments, the one or more chemical species is a biomolecule. In some embodiments, the biomolecule is chosen from one or more of a protein, an enzyme, an antibody, a peptide, a nucleic acid, an antidote and a vaccine. In some embodiments, the biomolecule is a vaccine. In some embodiments, the one or more biological species is a microorganism. In some embodiments, the microorganism is chosen from one or more of anaerobic bacteria, aerobic bacteria, mammalian cells, bacterial cells and viruses. In some embodiments, the microorganism is a virus. In some embodiments, the virus is a bacteriophage. In some embodiments, the virus is an enveloped virus. In some embodiments, the virus is a DNA virus. In some embodiments, the virus is Herpes Simplex Virus (HSV-2). In some embodiments, the virus is HSV-2 TK$^-$. In some embodiments, the virus is a RNA virus. In some embodiments, the virus is influenza virus. In some embodiments, the virus is PR8. In some embodiments, the virus is formulated for administration in a biological preparation. In some embodiments, the virus is formulated for administration as a live-attenuated vaccine. In some embodiments, the virus is formulated for administration as an inactivated vaccine.

In some embodiments, the polymer matrix further comprises one or more additional substances or additives such as, but not limited to, seasonings, spices, colorings, flavors, emulsifiers and plasticizers. In some embodiments, the physical properties of the polymer matrix, such as solubility, transparency, tactile impression, texture, plasticity, etc. are changed using additives.

III. Methods and Uses of the Application

The Applicants have found that chemical and/or biological species can be preserved and/or stabilized by incorporating the species within in a polymer matrix comprising certain amounts of pullulan and trehalose.

Accordingly, the present application includes a method of preserving and/or stabilizing one or more chemical and/or biological species comprising:
a) combining the one or more chemical and/or biological species, an aqueous solution comprising pullulan and an aqueous solution comprising trehalose to provide a mixture; and
b) drying the mixture to form a polymer matrix which preserves and/or stabilizes the one or more chemical and/or biological species.

In some embodiments, the trehalose is added to an aqueous solution of pullulan and the one or more chemical and/or biological species. In some embodiments, the trehalose is added at a concentration of about 0.1 to 1 M, or about 0.5 M.

In some embodiments, the one or more chemical and/or biological species, an aqueous solution comprising pullulan and an aqueous solution comprising trehalose are mixed thoroughly to ensure uniform distribution of all of the ingredients.

In some embodiments, one or more additional substances or additives such as, but not limited to, seasonings, spices, colorings, flavors, emulsifiers, and plasticizers are added to the mixture, and/or to the one or more chemical and/or biological species, the aqueous solution comprising pullulan or the aqueous solution comprising trehalose prior to drying. In some embodiments, the physical properties of the polymer matrix, such as solubility, transparency, tactile impression, texture, plasticity, etc. is changed using additives.

In some embodiments, the mixture is drop cast into a specific shape prior to drying. In some embodiments, the shape is a pill or a capsule.

In some embodiments, the mixture is formed into a film or is coated onto a substance or surface prior to drying. In some embodiments, the film or coating, is applied to food, or is used as food packaging. In some embodiments, the film or coating is used as a wound dressing. In some embodiments, the film or coating is used in a filter, such as in a water filter. In some embodiments, the mixture is formed into a thin film of any of a variety of shapes, for example a strip or patch. In some embodiments, the shaped object is a pill or capsule.

In some embodiments the polymer matrix comprises about 10 wt % to about 50 wt % of pullulan and about 50 wt % to about 90 wt % of trehalose, based on the dry weight of the matrix. In some embodiments the polymer matrix comprises about 20 wt % to about 40 wt % of pullulan and about 60 wt % to about 80 wt % of trehalose, based on the dry weight of the matrix. In some embodiments the polymer matrix comprises about 30 wt % to about 45 wt % of pullulan and about 60 wt % to about 70 wt % of trehalose, based on the dry weight of the matrix. In some embodiments the polymer matrix comprises about 37 wt % of pullulan and about 63 wt % of trehalose, based on the dry weight of the matrix.

In some embodiments the pullulan has a molecular weight in the range of about 100,000 to about 200,000. Pullulan having such molecular weights is commercially available, for example from Hayashibara Co, Ltd., Okayama, Japan. Trehalose is available from a variety of commercial sources, including, for example, Hayashibara Co, Ltd., Okayama, Japan. In some embodiments, for use in food products, the pullulan and trehalose are both food grade materials. In some embodiments, for use in medical products, the pullulan and trehalose are both medical grade, or pharmaceutically acceptable, materials.

In some embodiments, the one or more chemical and/or biological species are preserved and/or stabilized without requiring refrigeration. In some embodiments, one or more chemical or biological species are preserved at a temperature of from about 2° C. to about 40° C., about 10° C. to about 30° C. or about 20° C. to about 25° C. In an embodiment, the one chemical or biological species are preserved and/or stabilized for at least 3 months at the above temperatures.

In some embodiments, the one or more chemical species is a biomolecule. In some embodiments, the biomolecule is chosen from one or more of a protein, an enzyme, an antibody, a peptide, a nucleic acid, an antidote and a vaccine. In some embodiments, the biomolecule is a vaccine. In some embodiments, the one or more biological species is a microorganism. In some embodiments, the microorganism is chosen from one or more of anaerobic bacteria, aerobic bacteria, mammalian cells, bacterial cells and viruses. In some embodiments, the microorganism is a virus. In some embodiments, the virus is a bacteriophage. In some embodiments, the virus is an enveloped virus. In some embodiments, the virus is a DNA virus. In some embodiments, the virus is Herpes Simplex Virus (HSV-2). In some embodiments, the virus is HSV-2 TK$^-$. In some embodiments, the virus is a RNA virus. In some embodiments, the virus is influenza virus. In some embodiments, the virus is PR8. In some embodiments, the virus is formulated for administration in a biological preparation. In some embodiments, the virus is formulated for administration as a live-attenuated vaccine. In some embodiments, the virus is formulated for administration as an inactivated vaccine.

The following non-limiting examples are illustrative of the present application:

EXPERIMENTAL

Example 1

Materials

Pullulan (PI20 food grade, 200 kDa) was obtained from Hayashibara Co, Ltd., Okayama, Japan. D-(+)-trehalose dehydrate, D-(+)-maltose monohydrate, sucrose, calcium chloride ($CaCl_2$)), magnesium sulfate ($MgSO_4.7H_2O$), Tris, gelatin, Tryptic Soy Broth (TSB), and *Listeria* enrichment broth (LEB) were purchased from Sigma-Aldrich. Agar and agarose were purchased from Becton, Dickinson and Company (BD). Phosphate buffered saline (PBS) was purchased from BioShop Canada. *Listeria monocytogenes* serotype ½a, *E. coli* O157:H7, and *Salmonella* Newport, were routinely cultured and maintained in our lab. Two Myoviridae phages, *E. coli* O157:H7 phage, EcoM-AG10 (AG10), and *Salmonella* phage, SnpM-CG4-1 (CG4-1), were obtained from Canadian Research Institute for Food Safety, University of Guelph. LISTEX™ P100 was purchased from Micreos Food Safety (Wageningen, The Netherlands). Distilled deionized water was obtained from a Milli-Q Advantage A10 water purification system (EMD Millipore) and was autoclaved.

Film Formulation

*Listeria* phage films were made by mixing 100 μL of LISTEX™ P100 ($2\times10^{11}$ PFU/mL) with 900 μL of 11.1 wt % pullulan solution so that the final concentration of pullulan in the phage/pullulan mixture is 10 wt % and the phage concentration is $2\times10^{10}$ PFU/mL. For some experiments, a disaccharide (trehalose, maltose, or sucrose) was added to the phage/pullulan mixture at concentration of 0.5 M unless otherwise stated. The solution was mixed by repeated pipetting to ensure uniform distribution of all components. The phage films were formed by pipetting 100 μL of the phage/pullulan/sugar solution into individual wells of a 24-well plate and allowed to air dry for 24 hrs at room temperature. The titer of each phage stock was determined and the anticipated phage titer per film is $2\times10^9$ PFU for LISTEX™, $1\times10^7$ PFU for AG10 and $1\times10^8$ for CG4. The films were then stored under ambient conditions (~22-25° C.) with no humidity or temperature control for various lengths of time. A scheme showing the process for the preparation of phage films is presented in FIG. 1.

Quantification of Infectivity for Phage Embedded in the Films

The infectivity of phages encapsulated in dried films was quantified using the overlay technique.[80] The phage-containing film was dissolved in 1 mL of CM buffer (prepared by mixing 2.5 g $MgSO_4.7H_2O$, 0.735 g of $CaCl_2$), 0.05 g gelatin, and 6 mL 1 M Tris-HCl at pH 7.5, with water for a final volume of 1 L) through repeated pipetting. The reconstituted film solution was then serially diluted in CM buffer, each dilution was mixed in equal volumes with 100 μL of the bacterial host ($10^9$ CFU/mL) and then incubated at 30° C. for 10 minutes to allow for phage adsorption. The phage-host mixture was then added to 4 mL of soft Tryptic Soy Agar (TSA, prepared by adding 0.5% agarose to TSB) and overlayed onto a TSA plate (1.5% agar to TSB). The plates were incubated at 30° C. overnight. Plaque formation was observed the following day, and the plaques were counted to determine the phage titer of each film. For each dilution, triplicate experiments were conducted. The total number of plaques were averaged and considered as the number of viable phages.

Analysis of Phage Activity Loss Over Time

The loss of phage activity in the film was modeled using an exponential decay equation in the form of $A=A_0e^{-kt}$, where A is the phage titer at time t, $A_0$ is the initial phage titer, and k is the decay rate. The activity loss can be described using the activity loss time-constant, which is calculated as the inverse of the decay rate.

Phage Coating on Paper

Commercially available meat butcher paper (GTFrench Paper Limited, Hamilton, Canada) was used for phage coating experiments. The phage/sugar mixture was prepared as described earlier. Next, 1 mL of the phage/sugar mixture was spread uniformly onto a 12 cm by 12 cm area of a 21.6 cm by 27.9 cm sheet of paper using an EC-200 Variable Speed Drawdown Coater (ChemInstruments, OH, USA) with a size 40 EC-200 rod. The paper was air-dried overnight before being cut into 1 cm by 1 cm squares. The small pieces of the phage-coated papers were stored at ambient conditions. A scheme showing the process for the preparation of phage coatings is presented in FIG. 1.

Quantification of Phage Leaching from Paper

A 1×1 cm square of phage coated paper (from the above step) was placed in 1 mL CM buffer with occasional shaking at room temperature. A 100 µL aliquot of eluent was taken from the tube at different time points and transferred to a fresh tube for phage titer determination using the overlay technique, as described above. The data were used to determine the phage elution time that was then used for the subsequent experiments to test the infectivity of phages embedded in the films after different storage times.

Quantification of Antimicrobial Activity of Phage-Coated Paper

To test the infectivity of immobilized phage on paper, overlays of *Listeria* or *Salmonella* (overnight culture, 100 µL) in 4 mL of soft TSA was prepared on TSA plates and allowed to solidify at room temperature. Next, three 1×1 cm pieces of phage-coated paper were placed on the solidified agar surface with the phage layer facing the lawn and the plates were incubated at 30° C. overnight. The following day, the plates were inspected for lysis rings. The paper was then removed from the bacterial lawn to visualize the cleared zone produced by the phages. The dimensions of the clear zones were measured using a ruler.

The clear zones were individually excised, transferred into fresh micro-centrifuge tubes, crushed using a spatula, and eluted in 1 mL of PBS in the tube by shaking for 1 hr. A 100 µL aliquot of the eluent was then serially diluted in PBS, spread-plated onto *Listeria* Enrichment Agar plates for *Listeria* or Brilliant Green Agar plates for *Salmonella* and incubated at 30° C. for 48 hrs, after which the number of colonies on the plate were counted. These experiments were conducted in triplicate.

Results and Discussion

A coating comprised of pullulan and trehalose for long-term stabilization of phage antibacterials on food packaging was developed. The effectiveness of the coating was demonstrated against *E. coli*, *Salmonella*, and *Listeria*. The *Listeria* phage, Listex™ P100, is an FDA approved and commercially available bacteriophage, active against *Listeria monocytogenes*, whereas the other phages have been isolated from environmental samples in previous studies.

In this application, a coating that effectively preserved the antibacterial activity of three lytic phages against *Listeria monocytogenes*, *Salmonella* Newport and *E. coli* O157:H7 coated on food packaging was prepared and shown to be an effective and simple method for long term stabilization of bacteriophages by encapsulating them in sugar glasses composed of a mixture of pullulan and trehalose. The method may use drop casting which does not require access to specialized equipment, controlled storage conditions, or the need of a cold chain distribution system to maintain the coating's activity. Herein, it was shown that stabilizing bacteriophages under ambient conditions for prolonged periods of time cannot be achieved using films solely composed of pullulan. The films should also comprise trehalose. The combination of pullulan and trehalose in the same film creates a synergistic effect that leads to long-term stability of the bacteriophages. This may be a critical factor for the realization of phage antibacterials in the food industry, because many bacteriophages suffer an irreversible loss of infectivity once they dry out. Strategies have been reported for preserving phage infectivity during the freeze-drying process, but the methods described herein do not rely on freeze drying, do not require any specialized equipment for preparation or storage, and allow for preservation of phage antibacterial activity under ambient conditions. The encapsulated phages in the pullulan-trehalose coatings were able to retain their infectivity for up to 3 months when stored at ambient conditions. These films are water soluble, biocompatible, and comprised of components that are food-grade and FDA approved. Accordingly, the use of pullulan in combination with trehalose may be a promising method for preservation of bacteriophage antibacterial activity in a dried format. This technology has the potential to create highly stable phage-coated surfaces that can be used for food protection, food preparation, wound-dressings to prevent/control bacterial infections, and in point-of-use filtration systems for water purification.

Example 2

Methods

Pullulan and Trehalose Pill Preparation, Storage, and Reconstitution

Pills containing HSV-2, HSV-2 TK$^-$, or PR8 were prepared by mixing 1 µL of solution containing the virus with 9 µL of a solution containing 10 wt % Pullulan (Polysciences, 200 kDa) and 0.5 M trehalose (Sigma). For formalin-inactivated PR8, 50 μL of the inactivated virus was mixed with 50 μL of 10 wt % pullulan and 0.5 M trehalose. The mixture was then air dried in a 1.7 mL microcentrifuge tube overnight in a biological safety cabinet. After drying, the tubes were capped and wrapped in paraffin film. The wrapped tubes were then placed in a heating block and stored at 40° C. for up to 3 months. At each time point, a sample was removed from the heating block and reconstituted in PBS. The reconstituted sample was then used for titration for in vitro study or administered to a mouse for in vivo study. FIG. 9 shows a schematic of the process for pill preparation, storage, and reconstitution.

In-Vitro HSV-2 Viral Titration

Vero cells were grown in a monolayer to confluence in 12-well plates in alpha minimum essential medium (α-MEM) supplemented with 1% penicillin and streptomycin, 1% 1-glutamine, and 1% Hepes. Samples were resuspended and serially diluted ($10^{-1}$ to $10^{-6}$) in PBS and incubated with the monolayer for 2 h at 37° C. The vero cells were then overlaid with α-MEM supplemented with 0.05% human immune serum and incubated for 48 h at 37° C. After incubation, the cells were fixed and stained with crystal violet, and plaques were quantified using a light microscope. The PFU per pill was calculated using the plaque count and the corresponding dilution factor.

Genital HSV-2 Immunization and Infection

C57BL/6 (B6), 6-8-wk-old mice purchased from Charles River were used in the HSV-2 studies. The mice were housed at McMaster's Central Animal Facility (CAF) in pathogen-free conditions with a 12-h day and 12-h night cycle. All experiments were performed in accordance with Canadian Council on Animal Care guidelines and approved by the Animal Research Ethics Board at McMaster University. For the HSV-2 infection study, mice were injected subcutaneously with 2 mg Depo-Provera (medroxyprogesterone acetate) 5 days before HSV-2 infection. The mice were then infected intravaginally with 10 μL of the reconstituted HSV-2 sample. For the immunization experiments using $TK^-$ HSV-2. Mice were injected subcutaneously with 2 mg Depo-Provera (medroxyprogesterone acetate) 5 days prior to immunization. Mice were then immunized with 10 μL of the reconstituted HSV-2 $TK^-$. 9 days after immunization, the mice were injected subcutaneously with 2 mg Depo-Provera. 14 days after immunization, the mice were infected with HSV-2, 333 strain, at a dose of $10^5$ PFU per mouse. For both the infection study and immunization study the mice were assessed for genital pathology and survival. Genital pathology was scored on a scale of 5 according to severity of redness, swelling, lesion development, hair loss, ulceration, and lower limb paralysis. Ulceration of a lesion and/or lower limb paralysis was considered endpoint.

Influenza Virus Infection 6-8 week old BALB/c mice (Charles River Laboratories, Inc., Wilmington, Mass., USA) received either PBS, Influenza Virus A/PR/8/1934 (PR8) (initial titre $10^5$ PFU) stored at 40° C. for 12 weeks, PR8 (initial titre $10^5$ PFU) in combination with PT at 40° C. for 12 weeks, or 250 PFU PR8 stored at −80° C. Mice were anesthetised with isoflourane and inoculated with 20 uL per nostril, for a total volume of 40 uL per mouse. Weight was monitored for 14 days as a measure of morbidity. Weight loss and survival were analyzed using GraphPad Prism 7 (GraphPad Software, La Jolla, Calif., USA). Mice were euthanized after loss of 20% of initial body weight. All animal procedures were approved by the Animal Research Ethics Board of McMaster University.

Influenza Virus Vaccination 6-8 week old BALB/c mice (Charles River Laboratories, Inc., Wilmington, Mass., USA) were vaccinated i.m. in the left hind limb with PBS, formalin-inactivated PR8 stored at 40° C. for 12 weeks, formalin-inactivated PR8 stored at 40° C. in combination with PT for 12 weeks, or formalin-inactivated PR8 stored at −80° C. All vaccinations were administered in 100 uL volumes. 14 days post-vaccination mice were bled via the facial vein and blood was stored at 4° C. overnight. Following incubation overnight, blood was centrifuged at 16,000×g for 10 min at 4° C. to separate serum. 30 days post-vaccination mice were challenged with 250 PFU of PR8 per mouse, as described above, and monitored for weight loss as a measure of morbidity. Weight loss and survival were analyzed using GraphPad Prism 7 (GraphPad Software, La Jolla, Calif., USA). Mice were euthanized after loss of 20% of initial body weight. All animal procedures were approved by the Animal Research Ethics Board of McMaster University.

ELISA

Enzyme linked immunosorbent assays (ELISA) were performed in 96 well plates (ThermoFisher Scientific, Mississauga, ON, CA). Plates were coated with IgG capture antibody (ThermoFisher Scientific, Mississauga, ON, CA) or formalin-inactivated PR8 influenza virus at 2 µg/mL for 24 hours at 4° C. in bicarbonate/carbonate coating buffer (0.05M $Na_2CO_3$, 0.05M $NaHCO_3$, pH 9.4). Plates were then blocked using 100 µL of 5% non-fat milk in PBS with 0.1% tween (PBS-T) for 1 hour and room temperature (RT). Following blocking, serum samples were added at starting dilutions of 1:800 in blocking buffer for IgG wells and 1:50 for whole-inactivated virus-containing wells, and were diluted 1:2 across the plate 11 times, leaving the last well as a blank control. Samples were incubated for 1 hour at RT. Following the 1-hour incubation period, plates were washed 3 times with PBS-T, after which 100 uL of IgG-HRP (Santa Cruz Biotechnology, Inc., Dallas, Tex., USA) was added at 0.1 µg/mL, diluted in PBS-T, and incubated for 1 hour at room temperature. Following the incubation period, plates were washed 3 times with PBS-T and 100 µL of Sigmafast OPD substrate (MilliporeSigma, Oakville, ON, CA) was added for 10 minutes. The reaction was stopped with 50 µL of 3M HCl. Plates were then analyzed on the Spectramax i3 plate reader (Molecular Devices, Sunnyvale, Calif., USA) at an absorbance of 490 nm, data was then analyzed using GraphPad Prism 7 (GraphPad Software, La Jolla, Calif., USA). Data was transformed into a log(X) scale and a nonlinear fit was performed using the log(agonist) vs. response with a variable slope (four parameters). The area under the curve (A.U.C.) was then graphed and statistical analysis was performed using a one-way ANOVA with a Tukey post-hoc test.

Influenza Virus Quantification

PR8 viral titres were determined by plaque assay on MDCK cells. Titres were analyzed using GraphPad Prism 7 (GraphPad Software, La Jolla, Calif., USA).

Hemagglutinin Inhibition (HAI) Assay

Prior to performing the HAI assay, serum was pooled and subsequently inactivated. 0.5 volumes of 8 mg/mL TPCK-treated trypsin (MilliporeSigma, Oakville, ON, CA) was added to 1 volume of serum and incubated at 56° C. for 30 minutes. Following incubation, 3 volumes of 0.011 M metapotassium periodate (MilliporeSigma, Oakville, ON, CA) solution per volume of serum was added and incubated for 15 min at RT. Following incubation, 3 volumes of 1% glycerol saline solution was added and incubated at RT for another 15 minutes. Finally, 2.5 volumes of 0.85% saline was added to the serum. Inactivated serum samples were serially (2-fold) diluted across a 96 well plate (Fisher Scientific, Ottawa, ON, CA) at 25 uL/well. A dilution of PR8 virus sufficient to produce 3 wells of HA activity was added to all of the wells (25 uL/well) and incubated for 30 mins at RT to allow for antibody-virus neutralization. After incubation, 0.5% chicken red blood cells (Canadian Food Inspection Agency [CFIA], Nepean, ON, CA) was added to each well at 50 uL/well. The plate was then incubated at 4° C. for 45 minutes. HAI titre was graphed using GraphPad Prism 7 (GraphPad Software, La Jolla, Calif., USA).

Results

Pullulan and Trehalose (PT) Film Provides Thermal Protection for HSV-2 In Vitro

HSV-2, 333 strain was dried in three different drying matrices, 1) 10 wt % pullulan, 2) 0.5 M trehalose and 3) a mixture of 10 wt % pullulan with 0.5 M trehalose, to determine the stabilization effectiveness of the three solutions. Each sample had an initial titre of $2\times10^4$ plaque forming units (PFU) and was stored at room temperature (~23° C.). The titer of the three different dried samples were determined at different storage times and the results are shown in FIG. 10(A). HSV-2 dried in 10 wt % pullulan and 0.5 M trehalose was the most effective in maintaining viral titer. After 12 weeks, HSV-2 stored in pullulan/trehalose (PT) film had only a titer loss of 2.3 log PFU/film. In comparison, HSV-2 dried in 0.5 M trehalose had a titer loss of 3.6 log PFU/film after 12 weeks. HSV-2 dried in 10 wt % pullulan was completely inactive within 7 days, while HSV-2 stored in PBS buffer had was completely inactive within 28 days.

The results also show that pullulan by itself offers little protection against desiccation. HSV-2 dried in pullulan had a titre loss of 2.2 log PFU/film during the drying process. On the other hand, HSV-2 dried in trehalose alone or in pullulan and trehalose had a titre loss of 0.9 log PFU/film and 0.7 PFU/film respectively during the drying process. Moreover, drying HSV-2 in trehalose alone does not offer long-term stability. After four weeks, HSV-2 dried in trehalose alone had a titre loss of 2.4 log PFU/film while HSV dried in PT films had a titre loss of 1.0 log PFU/film. Furthermore, HSV-2 in PT film demonstrated good stability after two weeks of storage. After two weeks of storage, HSV-2 in PT film had a titre loss of 1.0 log PFU/film. However, between week 2 and week 12, there was only a loss of 0.3 log PFU/film. In comparison, HSV-2 dried in trehalose had a titre loss of 2.0 log PFU/film between week 2 and week 12.

This result shows that pullulan and trehalose have a synergistic effect as a stabilizing matrix and is similar to results achieved in stabilizing bacteriophages in sugar glasses as described in Example 1.[68]

Figure 10:
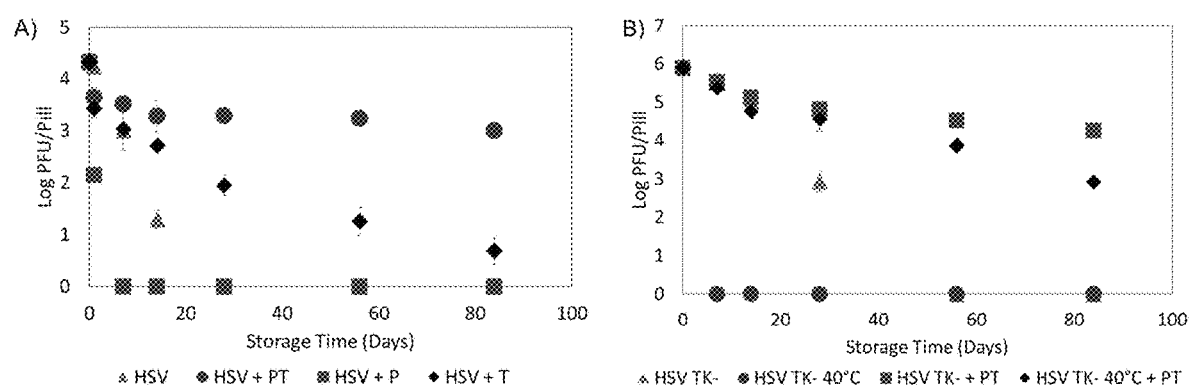
FIG. 10 shows in-vitro thermal stabilization of HSV-2 and HSV-2 TK$^-$: (A) Titre of HSV-2 stored in pullulan (P), trehalose (T), or exemplary pullulan and trehalose (PT) as a function of storage time at room temperature. (B) TK$^-$ HSV-2 and TK$^-$ HSV-2+PT titre as a function of storage time at room temperature and at 40° C. The in vitro experiments were performed in triplicates. The error bars represents the standard deviation.

To further study the thermal stabilizing capability of PT films at elevated temperature, live-attenuated HSV-2 TK$^-$ (initial titre, $10^6$ PFU) were dried in 10 wt % pullulan and 0.5 M trehalose and the samples were stored at room temperature and at 40° C. The titre were determined at different time points for up to 12 weeks and compared with HSV-2 TK$^-$ stored at the same temperatures. As FIG. 10(B) shows, HSV-2 TK$^-$ stored in PT films had a titre loss of 1.6 log PFU/film when stored at room temperature and a titre loss of 3.0 log PFU/film when stored at 40° C. In contrast, HSV-2 TK$^-$ without pullulan and trehalose was completely inactive within 8 weeks when stored at room temperature and was inactive within 1 week when stored at 40° C. Moreover, during the first 4 weeks, the storage temperature did not significantly affect the stability of HSV-2 TK$^-$ in PT films. However, at 8 weeks and 12 weeks, HSV-2 TK$^-$ in PT film was more stable at room temperature than at 40° C. Overall, these in vitro results demonstrate that PT films offer thermal protection for HSV-2 and HSV-2 Tk$^-$.

Figure 11:
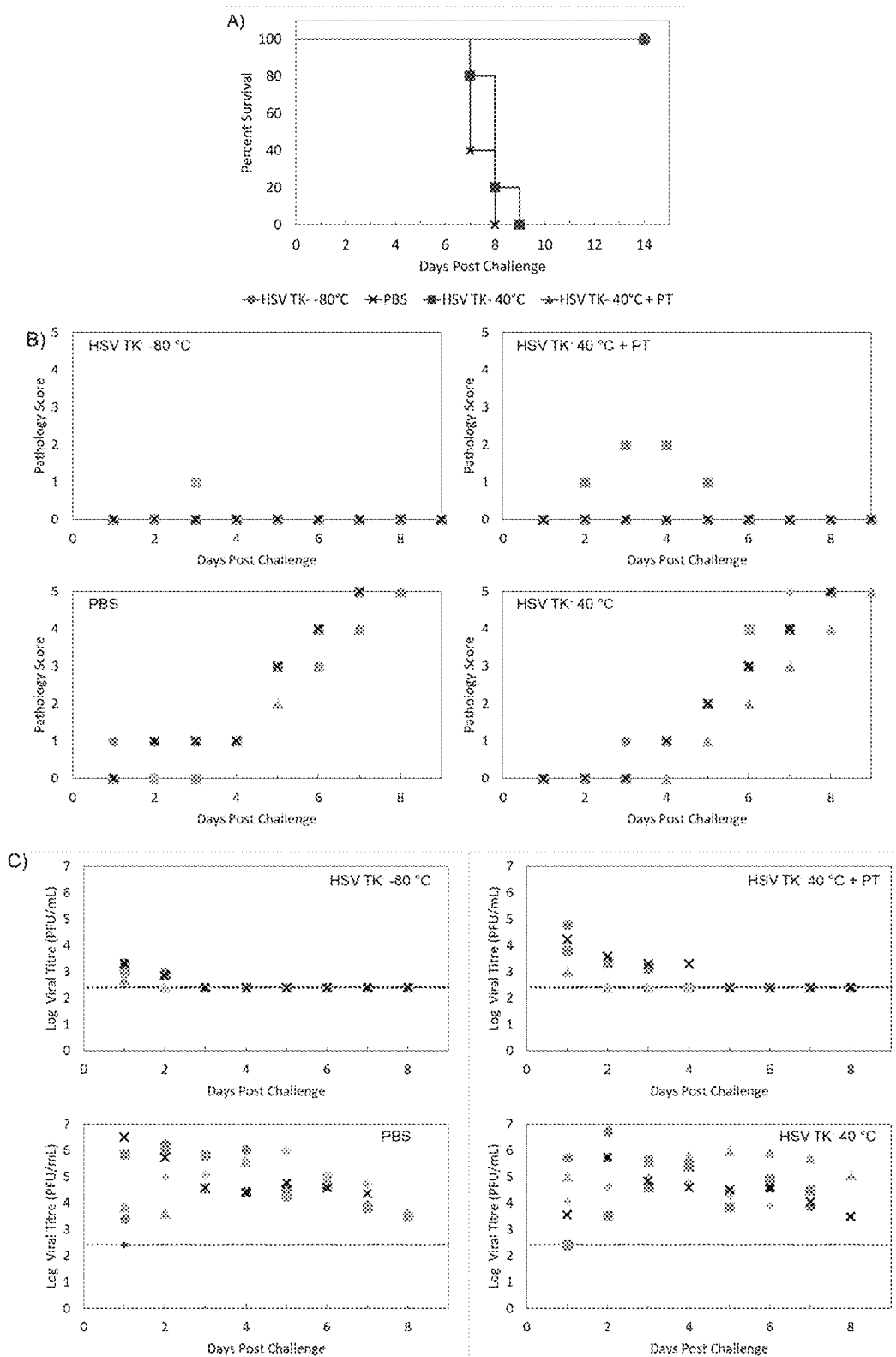
FIG. 11 shows (A) Survival curve of mice immunized with TK$^-$ HSV-2 and TK$^-$ HSV-2+ exemplary PT vaccine after 8 weeks of storage in exemplary compositions at 40° C. Five mice were used for each group. (B) Pathology scores of mice after infection with HSV-2. Each symbol represent a single mouse. The pathology scores are explained in Methods. (C) Viral titre of vaginal washes as a function of days post infection.

HSV-2 TK$^-$ Thermostabilized in PT Film Retains Immunogenicity at 40° C. for 8 Weeks After demonstrating the thermostabilizing ability of PT films on HSV-2 Tk$^-$ in vitro, the immunogenicity of HSV-2 TK$^-$ in PT films was determined in vivo. C57BL/6 mice were immunized intravaginally with 1) TK$^-$ stored at −80° C., 2) PBS, 3) TK$^-$ stored at 40° C. for 8 weeks, and 4) TK$^-$ dried in PT stored at 40° C. for 8 weeks. Five mice were immunized for each group. Since the in vitro results show that there is a decrease in titer over time in the PT films, the samples were prepared with a higher initial dose than the therapeutic dose. Each sample had an initial dose of $10^6$ PFU, whereas the therapeutic dose is $5 \times 10^4$ PFU. After the mice were inoculated with TK$^-$, they were challenged with a lethal dose of HSV-2 14 days after immunization. The survival curve is shown in FIG. 11(A). All mice treated with HSV-2 TK$^-$ in PT films survived the infection showing that it retained immunogenicity after 8 weeks at 40° C. Four of the five mice showed no visible signs of vaginal pathology. Only one mouse that was immunized with TK$^-$ in PT film showed minor signs of infection prior to recovering FIG. 11 (B). Viral titre of the vaginal washes correlated well with the pathology data FIG. 11 (C). Mice treated with Tk$^-$ in PT film resolved the infection within 5 days and no viral titre from the vaginal washes was detected subsequently. This is comparable to the mice immunized with fresh Tk$^-$. The mice immunized with fresh Tk$^-$ all survived and resolved the infection within 3 days. On the other hand, the mice that were immunized with TK$^-$ stored at 40° C. all showed signs of severe vaginal pathology and reached their clinical endpoint within 9 days. This is similar to the mice immunized with PBS (placebo) which all reached endpoint within 8 days. The results show that PT films was able to maintain the efficacy of live-attenuated HSV-2 Tk$^-$ despite prolonged exposure to elevated temperature.

Figure 12:
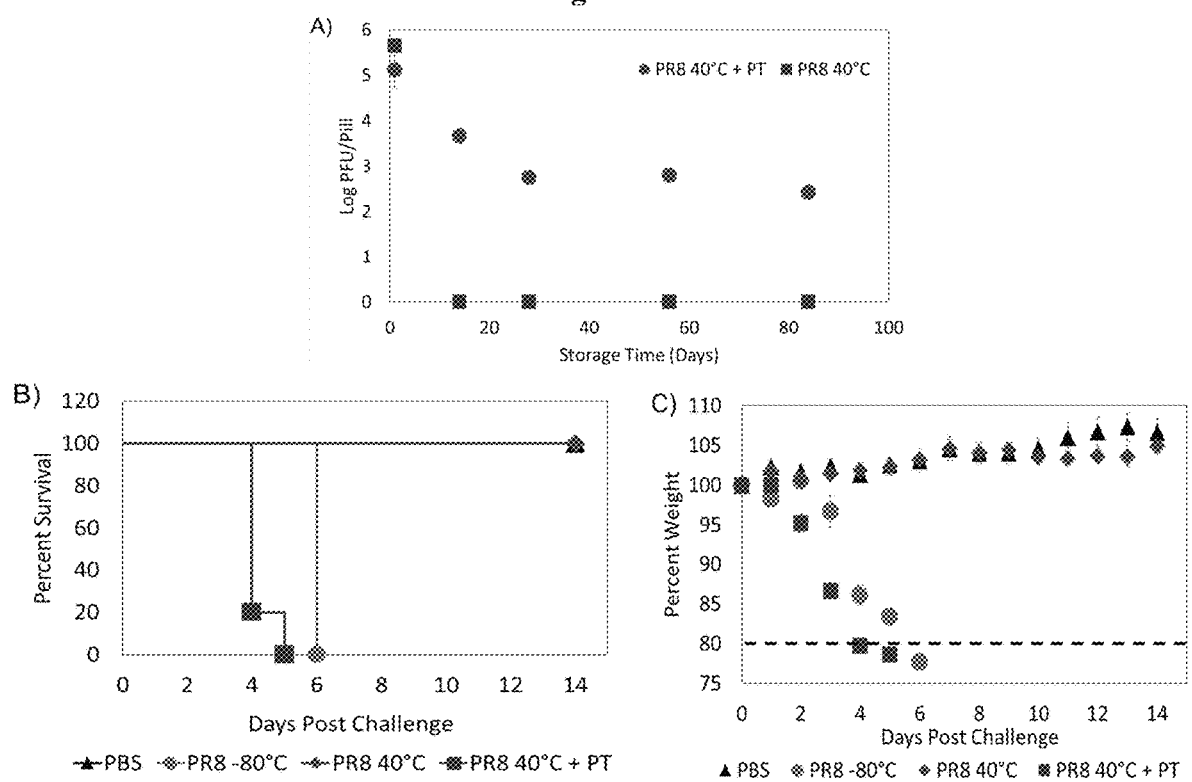
FIG. 12 shows thermal stability of PR8 in exemplary pullulan-trehalose films in vitro and in vivo. (A) Titre of PR8 and PR8+ exemplary PT versus storage time at 40° C. Experiments were performed in duplicates. Error bars indicate standard deviation. (B) Survival curve and (C) weight loss curve of mice infected with i) PBS; ii) PR8 stored at −80° C.; iii) PR8 stored at 40° C. for 12 weeks; iv) PR8 in exemplary PT film stored at 40° C. for 12 weeks.

PT Films Thermally Stabilize Live Influenza Virus PR8 In Vitro and Retains Infectivity In Vivo The results from the HSV-2 experiments demonstrated the thermal stabilizing ability of PT films on a DNA virus. Next the stabilizing effect of PT films on an RNA virus was investigated. Influenza virus, PR8, was dried in 10 wt % pullulan and 0.5 M trehalose and stored the samples at 40° C. over a period of 12 weeks. The titre of the samples were determined at different storage times and compared to PR8 stored at 40° C. FIG. 12(A) shows that PR8 stored at 40° C. was inactive within 14 days of storage while PR8 stored in PT only had a titre loss of 2.0 log PFU/film after 2 weeks. Similar to HSV-2, PR8 in PT films had a rapid loss in titre initially followed by a more gradual loss in titre. After 4 weeks of storage at 40° C. there was a titre loss of 2.9 log PFU/film. Between week 4 and week 12 there was only a titre loss of 0.3 log PFU/film. The total titre loss after 12 weeks of storage at 40° C., there was a titre loss of 3.2 log PFU/film for PR8 in PT films. The in vitro results show that PT films was able to offer thermal protection for PR8. However, PR8 was less thermally stable than HSV-2 and significant titre loss was observed within the first 4 weeks. PR8 in PT films was further test in vivo to determine the infectivity of the dried virus. Balb/C mice were infected intranasally with 1)PR8 stored at −80° C., 2) PBS, 3) PR8 stored at 40° C. for 12 weeks, and 4) PR8 dried in PT and stored at 40° C. for 12 weeks. The initial dose of the samples was $10^5$ PFU/mouse. FIGS. 12(B) and (C) show that the mice that were infected with PR8 in PT films had similar response to the infection when compared with mice infected with fresh PR8. The mice experience significant weight loss and reached clinical endpoint within 5 days for mice infected with PR8 in PT films and within 6 days for mice infected with fresh PR8. In contrast, the mice that were infected with PR8 stored at 40° C. did not experience any weight loss and did not show any clinical signs of infection. This demonstrates that PR8 in PT films were still able to infect even after being stored at 40° C. for 12 weeks. On the other hand, PR8 without PT was completely inactivated and was unable to infect.

Figure 13:
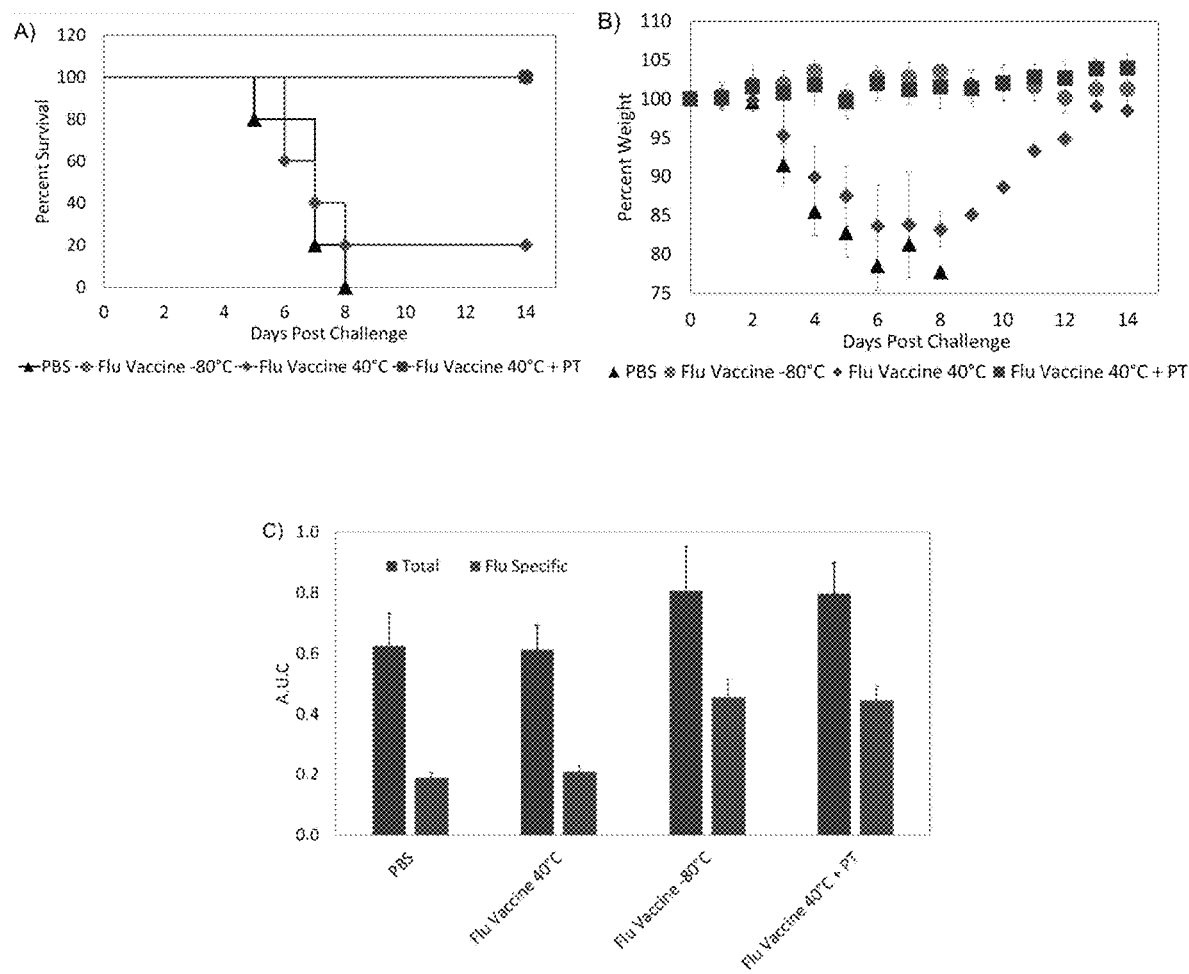
FIG. 13 shows in vivo results of inactivated PR8 vaccine after 12 weeks of storage in exemplary compositions at 40° C. (A) Survival curve and (B) percent weight versus days post infection for mice immunized with inactivated PR8 and inactivated PR8+ exemplary PT after 12 weeks of storage at 40° C. (C) Area under curve of ELISA assay for total IgG and flu specific IgG for serum samples taken from mice immunized with inactivated PR8 and inactivated PR8+ exemplary PT after 12 weeks of storage at 40° C. Five mice were used for each group.

Inactivated Influenza Vaccine Thermostabilzed in PT Film Retain Immmunogenicity at 40° C. for 12 Weeks The experiments shown above demonstrate that PT films are able to thermally stabilize live viruses (HSV2 and PR8) while maintaining their infectivity or immunogenicity in vivo. To further demonstrate the ability of PT to thermally stabilize inactivated viral vaccines, a formalin-inactivated PR8 was dried in PT films and the films were stored at 40° C. for 12 week. Balc/C Mice were immunized with 1) fresh vaccine (stored at −80° C.), 2) PBS, 3) inactivated PR8 stored at 40° C. for 12 weeks, and 4) inactivated PR8 dried in PT stored at 40° C. for 12 weeks. The initial dose of each sample was twice the therapeutic dose to account for loss in activity during the drying process and storage. Mice that were immunized with the vaccine in PT film stored at 40° C. did not show any clinical difference when compared to mice that were immunized with fresh vaccine. All mice in both groups survived 14 days after infection (FIG. 13(A)) and did not exhibit any weight loss (FIG. 13(B)). In contrast, four out of five mice that were vaccinated with the vaccine stored at 40° C. reached clinical endpoint (>20% weight loss) within 7 days post infection. The one mouse that did not reach endpoint still experienced significant weight loss (>15%) before recovering. The mice that were given placebo (PBS) all reached clinical endpoint 8 days after infection.

To further investigate the immunogenicity of the vaccines, blood samples were taken from the mice 14 days after immunization to determine the immune response and antibody production induced by the vaccine. The total IgG and flu-specific IgG were quantified by ELISA. Mice that were immunized with the vaccine in PT film had a significantly higher level of flu-specific IgG when compared with mice that were immunized with the vaccine stored at 40° C. (FIG. 13 (C)). Moreover, there was no significant difference in the level of flu-specific IgG between the mice immunized with fresh vaccine and the mice immunize with vaccine in PT film. This shows that the vaccine dried in PT films was able to induce the production of flu-specific antibodies in mice and provide protection against influenza infection even after being stored at 40° C. for 12 weeks. In contrast, the vaccine without PT after 12 weeks of storage at 40° C. did not exhibit any immunogenicity. The mice immunized with vaccine without PT had the same level of flu-specific IgG as mice immunized with PBS. This result was further confirmed by hemagglutination inhibition (HAI) assay of the serum. HAI assay showed that mice immunized with vaccine dried in PT had a HAI titre of 32 and mice immunized with fresh vaccine had a HAI titre of 6. On the other hand, mice immunized with the vaccine stored at 40° C. and mice immunized with PBS both had a HAI titre of 0. The HAI assay shows that vaccine in PT was able to generate a greater immunoresponse in mice compared to the fresh vaccine. This might be due to the fact that the initial dose of the vaccine in PT film was twice the therapeutic does. Nonetheless, this demonstrates that inactivated PR8 in PT films exhibit excellent thermal stability and was able to maintain vaccine potency for 12 weeks at 40° C.

Discussion

In this example, a simple and low-cost method to thermally stabilize two enveloped viruses: Herpes Simplex Virus (HSV-2), a DNA virus, and influenza virus (PR8), an RNA virus, by drying the viruses in a pullulan and trehalose mixture was investigated. As shown above pullulan and trehalose when used together can provide long-term stabilization for enzymes and bacteriophages by protecting them against oxidation and thermal inactivation.[83] Live enveloped viruses were chosen for this study because they are intrinsically more unstable than other types of vaccines, especially RNA viruses.[55, 58]

The development of thermally stable vaccines is crucial for the realization of universal immunization. Herein a cost-effective and simple platform for thermo-stable vaccines has been shown. It has been shown that drying vaccines in pullulan and trehalose, which are inexpensive and FDA approved, extends the shelf-life of the vaccine outside of the cold chain. It was demonstrated that this method can thermally stabilize a DNA virus (HSV-2), an RNA virus (Influenza PR8), a live-attenuated vaccine (HSV-2 $TK^-$) and an inactivated viral vaccine (formalin-inactivated PR8) for up to 12 weeks at 40° C. Moreover, it was shown that PT films do not interfere with the in vivo infectivity or immunogenicity of the viruses and vaccines.

The in vitro experiments showed that pullulan and trehalose together offered better thermal stability than using pullulan alone or trehalose alone. In was observed that using pullulan alone as the stabilizer was unable to protect the virus during desiccation and using trehalose alone as the stabilizer offered poor long-term stability. From these observations, without being limited by theory, a possible explanation for the synergistic behavior for the combination of pullulan and trehalose is that trehalose provides protection during desiccation while pullulan offers long-term stability by immobilizing the viruses in a glassy matrix.

The in vitro experiments also show that a significant decrease in viral titre takes place within the first 4 weeks of storage and then the viral titre remains relatively stable for up to 12 weeks. This may suggest that there are multiple degradation mechanisms within the PT films. Although the rate of titre loss for samples stored in PT films is much lower than samples stored in solution, there is still a loss in titre over time. Thus, there may be a need for higher initial dosing to compensate for the activity loss. Optimizing the formulation, preparation and storage conditions of the PT films as shown in Example 1 may improve the long-term stability of bacteriophages in PT films.[68]

While there was a loss in titre for live viruses in PT films, there was no observable loss in efficacy for inactivated PR8 viral vaccine in PT films. Thus, although PT films may be further optimized for live-attenuated vaccines, the in vivo results show that PT films can afford long-term stability for inactivated vaccines without further optimization.

In addition to thermal stabilization, drying vaccines in PT film may provide ease of administration for certain applications. Since pullulan is a good film forming agent that is water soluble, it is possible to administer vaccines in PT films directly in a film format without reconstitution. This is especially useful for vaccines that enter the body through mucosal surfaces such as oral or vaginal administration. The use of vaccine films can minimize storage space required and increase the ease of administration since it does not require reconstitution and needles.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Film Components | Decay Time Constant (Days) | One Day Decrease (log PFU/film) | Four Weeks Decrease (log PFU/film) | Eight Weeks Decrease (log PFU/film) |
|---|---|---|---|---|
| 0.1M Trehalose + 10% pullulan | 5.00 | 0.22 | 3.52 | 5.24 |
| 0.25M Trehalose + 10% pullulan | 5.10 | 0.19 | 3.55 | 4.92 |
| 0.5M Trehalose + 10% pullulan | 8.93 | 0.05 | 1.19 | 2.86 |
| 1M Trehalose + 10% pullulan | 2.90 | 0.77 | 5.39 | 9.00 |
| 0.5M Sucrose + 10% pullulan | 5.18 | 1.40 | 4.28 | 6.01 |
| 0.5M Maltose + 10% pullulan | 3.47 | 0.32 | 3.80 | 7.10 |
| 0.5M Trehalose + 10% pullulan in PBS | 0.33 | 1.15 | 9.00 | 9.00 |
| 0.5M Trehalose + 10% pullulan in CM | 8.85 | 0.09 | 1.28 | 3.15 |

TABLE 1-continued

| Film Components | Decay Time Constant (Days) | One Day Decrease (log PFU/film) | Four Weeks Decrease (log PFU/film) | Eight Weeks Decrease (log PFU/film) |
| --- | --- | --- | --- | --- |
| 10% pullulan | 0.40 | 1.42 | 9.00 | 9.00 |
| 0.5M Trehalose (no pullulan) | 9.09 | 1.33 | 4.44 | 6.23 |
| 0.5M Sucrose (no pullulan) | 9.71 | 2.92 | 4.19 | 7.26 |
| 0.5M Maltose (no pullulan) | 5.78 | 1.93 | 5.15 | 9.00 |
| Water (no pullulan) | 0.05 | 9.00 | 9.00 | 9.00 |

FULL CITATION FOR DOCUMENTS REFERRED TO IN THE SPECIFICATION (1) Smith, H. W.; Huggins, M. B. Successful Treatment of Experimental *Escherichia coli* Infections in Mice Using Phage: its General Superiority over Antibiotics. *Microbiology* 1982, 128 (2), 307-318 DOI: 10.1099/00221287-128-2-307.

(2) Kutateladze, M. Experience of the Eliava Institute in bacteriophage therapy. *Virol. Sin.* 2015, 30 (1), 80-81 DOI: 10.1007/s12250-014-3557-0.

(3) Ye, J.; Kostrzynska, M.; Dunfield, K.; Warriner, K. Evaluation of a biocontrol preparation consisting of *Enterobacter asburiae* JX1 and a lytic bacteriophage cocktail to suppress the growth of *Salmonella* Javiana associated with tomatoes. *J. Food Prot.* 2009, 72 (11), 2284-2292.

(4) Sharma, M.; Patel, J. R.; Conway, W. S.; Ferguson, S.; Sulakvelidze, A. Effectiveness of bacteriophages in reducing *Escherichia coli* O157:H7 on fresh-cut cantaloupes and lettucet. *J. Food Prot.* 2009, 72 (7), 1481-1485.

(5) Abuladze, T.; Li, M.; Menetrez, M. Y.; Dean, T.; Senecal, A.; Sulakvelidze, A. Bacteriophages reduce experimental contamination of hard surfaces, tomato, spinach, broccoli, and ground beef by *Escherichia coli* O157:H7. *Appl. Environ. Microbiol.* 2008, 74 (20), 6230-6238 DOI: 10.1128/AEM.01465-08.

(6) Spricigo, D. A.; Bardina, C.; Cortés, P.; Llagostera, M. Use of a bacteriophage cocktail to control *Salmonella* in food and the food industry. *Int. J. Food Microbiol.* 2013, 165 (2), 169-174 DOI: 10.1016/j.ijfoodmicro.2013.05.009.

(7) Anany, H.; Chen, W.; Pelton, R.; Griffiths, M. W. Biocontrol of *Listeria monocytogenes* and *Escherichia coli* O157:H7 in meat by using phages immobilized on modified cellulose membranes. *Appl. Environ. Microbiol.* 2011, 77 (18), 6379-6387 DOI: 10.1128/AEM.05493-11.

(8) Lone, A.; Anany, H.; Hakeem, M.; Aguis, L.; Avdjian, A.-C.; Bouget, M.; Atashi, A.; Brovko, L.; Rochefort, D.; Griffiths, M. W. Development of prototypes of bioactive packaging materials based on immobilized bacteriophages for control of growth of bacterial pathogens in foods. *Int. J. Food Microbiol.* 2016, 217, 49-58 DOI: 10.1016/j.ijfoodmicro.2015.10.011.

(9) Seo, J.; Seo, D. J.; Oh, H.; Jeon, S. B.; Oh, M.; Choi, C. Inhibiting the Growth of *Escherichia coli* O157: H7 in Beef, Pork, and Chicken Meat using a Bacteriophage. 2016, 36 (2), 186-193 DOI: 10.5851/kosfa.2016.36.2.186.

(10) Carocho, M.; Morales, P.; Ferreira, I. C. F. R. Natural food additives: Quo vadis? *Trends Food Sci. Technol.* 2015, 45 (2), 284-295 DOI: 10.1016/j.tifs.2015.06.007.

(11) Janež N.; Loc-Carrillo, C. Use of phages to control campylobacter spp. *J. Microbiol. Methods* 2013, 95 (1), 68-75 DOI: 10.1016/j.mimet.2013.06.024.

(12) Hudson, J. A.; Billington, C.; Carey-Smith, G.; Greening, G. Bacteriophages as biocontrol agents in food. *J. Food Prot.* 2005, 68 (2), 426-437.

(13) Mahony, J.; McAuliffe, O.; Ross, R. P.; van Sinderen, D. Bacteriophages as biocontrol agents of food pathogens. *Curr. Opin. Biotechnol.* 2011, 22 (2), 157-163 DOI: 10.1016/j.copbio.2010.10.008.

(14) Cademartiri, R.; Anany, H.; Gross, I.; Bhayani, R.; Griffiths, M.; Brook, M. a. Immobilization of bacteriophages on modified silica particles. *Biomaterials* 2010, 31 (7), 1904-1910 DOI: 10.1016/j.biomaterials.2009.11.029.

(15) Choińska-Pulit, A.; Mitula, P.; Śliwka, P.; Laba, W.; Skaradzińska, A. Bacteriophage encapsulation: Trends and potential applications. Trends *Food Sci. Technol.* 2015, 45 (2), 212-221 DOI: 10.1016/j.tifs.2015.07.001.

(16) Vonasek, E.; Le, P.; Nitin, N. Encapsulation of bacteriophages in whey protein films for extended storage and release. *Food Hydrocoll.* 2014, 37, 7-13 DOI: 10.1016/j.foodhyd.2013.09.017.

(17) Shea, K. M. Antibiotic Resistance: What Is the Impact of Agricultural Uses of Antibiotics on Children's Health? *Pediatrics* 2003, 112 (1), 253-258 DOI: 10.1542/peds.112.1.S1.253.

(18) Lau, C. H.-F.; van Engelen, K.; Gordon, S.; Renaud, J.; Topp, E. Novel Antibiotic Resistance Determinants from Agriculturual Soil Exposed to Antibiotics Widely Used in Human Medicine and Animal Farming. *Appl. Environ. Microbiol.* 2017, No. June, AEM.00989-17 DOI: 10.1128/AEM.00989-17.

(19) Azeredo, J.; Sutherland, I. The Use of Phages for the Removal of Infectious Biofilms. *Curr. Pharm. Biotechnol.* 2008, 9 (4), 261-266 DOI: 10.2174/138920108785161604.

(20) Jonczyk, E.; Kłak, M.; Miedzybrodzki, R.; Górski, A. The influence of external factors on bacteriophages—review. *Folia Microbiol. (Praha).* 2011, 56 (3), 191-200 DOI: 10.1007/s12223-011-0039-8.

(21) Puapermpoonsiri, U.; Spencer, J.; van der Walle, C. F. A freeze-dried formulation of bacteriophage encapsulated in biodegradable microspheres. *Eur. J. Pharm. Biopharm.* 2009, 72 (1), 26-33 DOI: 10.1016/j.ejpb.2008.12.001.

(22) Puapermpoonsiri, U.; Ford, S. J.; van der Walle, C. F. Stabilization of bacteriophage during freeze drying. *Int. J. Pharm.* 2010, 389 (1-2), 168-175 DOI: 10.1016/j.ijpharm.2010.01.034.

(23) Balcão, V. M.; Barreira, S. V. P.; Nunes, T. M.; Chaud, M. V.; Tubino, M.; Vila, M. M. D. C. Carbohydrate Hydrogels with Stabilized Phage Particles for Bacterial Biosensing: Bacterium Diffusion Studies. *Appl. Biochem. Biotechnol.* 2014, 172 (3), 1194-1214 DOI: 10.1007/s12010-013-0579-2.

(24) Dini, C.; Islan, G. A.; de Urraza, P. J.; Castro, G. R. Novel biopolymer matrices for microencapsulation of phages: Enhanced protection against acidity and protease activity. *Macromol. Biosci.* 2012, 12 (9), 1200-1208 DOI: 10.1002/mabi.201200109.

(25) Moghtader, F.; Eğri, S.; Piskin, E. Phages in modified alginate beads. *Artif. Cells, Nanomedicine, Biotechnol.* 2017, 45 (2), 357-363 DOI: 10.3109/21691401.2016.1153485.

(26) Kim, S.; Jo, A.; Ahn, J. Application of chitosan-alginate microspheres for the sustained release of bacteriophage in simulated gastrointestinal conditions. *Int. J. Food Sci. Technol.* 2015, 50 (4), 913-918 DOI: 10.1111/ijfs.12736.

(27) Colom, J.; Cano-Sarabia, M.; Otero, J.; Ariñez-Soriano, J.; Cortés, P.; Maspoch, D.; Llagostera, M. Microencapsulation with alginate/CaCO3: A strategy for improved phage therapy. *Sci. Rep.* 2017, 7 (December 2016), 41441 DOI: 10.1038/srep41441.

(28) Ma, Y.; Pacan, J. C.; Wang, Q.; Sabour, P. M.; Huang, X.; Xu, Y. Enhanced alginate microspheres as means of oral delivery of bacteriophage for reducing *Staphylococcus aureus* intestinal carriage. *Food Hydrocoll.* 2012, 26 (2), 434-440 DOI: 10.1016/j.foodhyd.2010.11.017.

(29) Dini, C.; Islan, G. A.; Castro, G. R. Characterization and Stability Analysis of Biopolymeric Matrices Designed for Phage-Controlled Release. *Appl. Biochem. Biotechnol.* 2014, 174 (6), 2031-2047 DOI: 10.1007/s12010-014-1152-3.

(30) Tang, Z.; Huang, X.; Baxi, S.; Chambers, J. R.; Sabour, P. M.; Wang, Q. Whey protein improves survival and release characteristics of bacteriophage Felix O1 encapsulated in alginate microspheres. *Food Res. Int.* 2013, 52 (2), 460-466 DOI: 10.1016/j.foodres.2012.12.037.

(31) Colom, J.; Cano-Sarabia, M.; Otero, J.; Cort??s, P.; Maspoch, D.; Llagostera, M. Liposome-encapsulated bacteriophages for enhanced oral phage therapy against *Salmonella* spp. *Appl. Environ. Microbiol.* 2015, 81 (14), 4841-4849 DOI: 10.1128/AEM.00812-15.

(32) Singla, S.; Harjai, K.; Katare, O. P.; Chhibber, S. Encapsulation of bacteriophage in liposome accentuates its entry in to macrophage and shields it from neutralizing antibodies. *PLoS One* 2016, 11 (4), 1-16 DOI: 10.1371/journal.pone.0153777.

(33) Korehei, R.; Kadla, J. F. Encapsulation of T4 bacteriophage in electrospun poly(ethylene oxide)/cellulose diacetate fibers. *Carbohydr. Polym.* 2014, 100, 150-157 DOI: 10.1016/j.carbpol.2013.03.079.

(34) Merabishvili, M.; Vervaet, C.; Pirnay, J.; Vos, D. De; Verbeken, G.; Mast, J.; Chanishvili, N.; Vaneechoutte, M. Stability of *Staphylococcus aureus* Phage ISP after Freeze-Drying (Lyophilization). *PLoS One* 2013, 8 (7), 1-7 DOI: 10.1371/journal.pone.0068797.

(35) Matthias, D. M., Robertson, J., Garrison, M. M., Newland, S. & Nelson, C. Freezing temperatures in the vaccine cold chain: A systematic literature review. *Vaccine* 25, 3980-3986 (2007).

(36) Levin, A., Levin, C., Kristensen, D. & Matthias, D. An economic evaluation of thermostable vaccines in Cambodia, Ghana and Bangladesh. *Vaccine* 25, 6945-6957 (2007).

(37) Favin, M., Steinglass, R., Fields, R., Banerjee, K. & Sawhney, M. Why children are not vaccinated: A review of the grey literature. *Int. Health* 4, 229-238 (2012).

(38) Luzze, H. et al. Understanding the policy environment for immunization supply chains: Lessons learned from landscape analyses in Uganda and Senegal. *Vaccine* 35, 2141-2147 (2017).

(39) Azimi, T., Franzel, L. & Probst, N. Seizing market shaping opportunities for vaccine cold chain equipment. *Vaccine* 35, 2260-2264 (2017).

(40) Sun, T. et al. Thermal stability of self-assembled peptide vaccine materials. *Acta Biomater.* 30, 62-71 (2016).

(41) Konar, M., Pajon, R. & Beernink, P. T. A meningococcal vaccine antigen engineered to increase thermal stability and stabilize protective epitopes. *Proc. Natl. Acad. Sci.* 112, 14823-14828 (2015).

(42) Rossi, R., Konar, M. & Beernink, P. T. Meningococcal factor H binding protein vaccine antigens with increased thermal stability and decreased binding of human factor H. *Infect. Immun.* 84, 1735-1742 (2016).

(43) Campeotto, I. et al. One-step design of a stable variant of the malaria invasion protein RH5 for use as a vaccine immunogen. *Proc. Natl. Acad. Sci.* 114, 998-1002 (2017).

(44) Stobart, C. C. et al. A live RSV vaccine with engineered thermostability is immunogenic in cotton rats despite high attenuation. *Nat. Commun.* 7, 1-12 (2016).

(45) Wang, G. et al. Rational design of thermostable vaccines by engineered peptide-induced virus self-biomineralization under physiological conditions. 1-6 (2013). doi: 10.1073/pnas.1300233110

(46) Pelliccia, M. et al. Additives for vaccine storage to improve thermal stability of adenoviruses from hours to months. *Nat. Commun.* 7, 1-7 (2016).

(47) Chu, L. Y. et al. Enhanced Stability of Inactivated Influenza Vaccine Encapsulated in Dissolving Microneedle Patches. *Pharm. Res.* 33, 868-878 (2016).

(48) Choi, H.-J. et al. Stability of influenza vaccine coated onto microneedles. *Biomaterials* 33, 3756-3769 (2012).

(49) Mistilis, M. J. et al. Long-term stability of influenza vaccine in a dissolving microneedle patch. *Drug Deliv. Transl. Res.* 7, 195-205 (2017).

(50) Hassett, K. J. et al. Glassy-State Stabilization of a Dominant Negative Inhibitor Anthrax Vaccine Containing Aluminum Hydroxide and Glycopyranoside Lipid A Adjuvants. *J. Pharm. Sci.* 104, 627-639 (2015).

(51) Hassett, K. J. K. et al. Stabilization of a recombinant ricin toxin A subunit vaccine through lyophilization. *Eur. J. Pharm. Biopharm.* 85, 279-86 (2013).

(52) Chen, D. et al. Thermostable formulations of a hepatitis B vaccine and a meningitis A polysaccharide conjugate vaccine produced by a spray drying method. *Vaccine* 28, 5093-5099 (2010).

(53) Ohtake, S. et al. Room temperature stabilization of oral, live attenuated *Salmonella enterica* serovar Typhi-vectored vaccines. *Vaccine* 29, 2761-71 (2011).

(54) Ohtake, S. et al. Heat-stable measles vaccine produced by spray drying. *Vaccine* 28, 1275-84 (2010).

(55) Lovalenti, P. M. et al. Stabilization of live attenuated influenza vaccines by freeze drying, spray drying, and foam drying. *Pharm. Res.* 33, 1144-1160 (2016).

(56) Madan, M. et al. Rational design of heat stable lyophilized rotavirus vaccine formulations. *Hum. Vaccin. Immunother.* 5515, 1-10 (2018).

(57) Naik, S. P. et al. Stability of heat stable, live attenuated Rotavirus vaccine (ROTASIIL®). *Vaccine* 35, 2962-2969 (2017).

(58) Alcock, R. et al. Long-Term Thermostabilization of Live Poxviral and Adenoviral Vaccine Vectors at Supraphysiological Temperatures in Carbohydrate Glass. *Sci. Transl. Med.* 2, 19ra12-19ra12 (2010)

(59) Wu, S.; Chen, J. Using pullulan-based edible coatings to extend shelf-life of fresh-cut "Fuji" apples. *Int. J. Biol. Macromol.* 2013, 55, 254-257 DOI: 10.1016/j.ijbiomac.2013.01.012.
(60) Farris, S.; Introzzi, L.; Fuentes-Alventosa, J. M.; Santo, N.; Rocca, R.; Piergiovanni, L. Self-Assembled Pullulan-Silica Oxygen Barrier Hybrid Coatings for Food Packaging Applications. *J. Agric. Food Chem.* 2012, 60 (3), 782-790 DOI: 10.1021/jf204033d.
(61) Wu, S. & Chen, J. Using pullulan-based edible coatings to extend shelf-life of fresh-cut 'Fuji' apples. *Int. J. Biol. Macromol.* 55, 254-257 (2013).
(62) Treviño-Garza, M. Z., García, S., del Socorro Flores-González, M. & Arévalo-Niño, K. Edible Active Coatings Based on Pectin, Pullulan, and Chitosan Increase Quality and Shelf Life of Strawberries (Fragaria *ananassa*). *J. Food Sci.* 80, M1823-M1830 (2015).
(63) Kraśniewska, K. et al. Effect of Pullulan Coating on Postharvest Quality and Shelf-Life of Highbush Blueberry (*Vaccinium corymbosum* L.). *Materials (Basel)*. 10, 965 (2017).
(64) Morsy, M. K., Sharoba, A. M., Khalaf, H. H., El-Tanahy, H. H. & Cutter, C. N. Efficacy of Antimicrobial Pullulan-Based Coating to Improve Internal Quality and Shelf-Life of Chicken Eggs During Storage. *J. Food Sci.* 80, M1066-M1074 (2015).
(65) Farris, S. et al. Self-Assembled Pullulan-Silica Oxygen Barrier Hybrid Coatings for Food Packaging Applications. *J. Agric. Food Chem.* 60, 782-790 (2012).
(66) Jahanshahi-Anbuhi, S.; Kannan, B.; Leung, V.; Pennings, K.; Liu, M.; Carrasquilla, C.; White, D.; Li, Y.; Pelton, R. H.; Brennan, J. D.; et al. Simple and ultrastable all-inclusive pullulan tablets for challenging bioassays. *Chem. Sci.* 2016, 7, 2342-2346 DOI: 10.1039/C5SC04184H.
(67) Jahanshahi-Anbuhi, S.; Pennings, K.; Leung, V.; Liu, M.; Carrasquilla, C.; Kannan, B.; Li, Y.; Pelton, R.; Brennan, J. D.; Filipe, C. D. M. Pullulan Encapsulation of Labile Biomolecules to Give Stable Bioassay Tablets. *Angew. Chemie Int. Ed.* 2014, 53 (24), 6155-6158 DOI: 10.1002/anie.201403222.
(68) Jain, N. K.; Roy, I. Effect of trehalose on protein structure. *Protein Sci.* 2008, No. September 2008, 24-36 DOI: 10.1002/pro.3.
(69) Tapia, H.; Koshland, D. E. Trehalose Is a Versatile and Long-Lived Chaperone for Desiccation Tolerance. *Curr. Biol.* 2014, 24, 2758-2766 DOI: 10.1016/j.cub.2014.10.005.
(70) Iyer, P. V.; Ananthanarayan, L. Enzyme stability and stabilization—Aqueous and non-aqueous environment. *Process Biochem.* 2008, 43 (10), 1019-1032 DOI: 10.1016/j.procbio.2008.06.004.
(71) Ohtake, S.; Wang, Y. J. Trehalose: Current use and future applications. *J. Pharm. Sci.* 2011, 100 (6), 2020-2053 DOI: 10.1002/jps.22458.
(72) Vandenheuvel, D.; Meeus, J.; Lavigne, R.; Van Den Mooter, G. Instability of bacteriophages in spray-dried trehalose powders is caused by crystallization of the matrix. *Int. J. Pharm.* 2014, 472 (1-2), 202-205 DOI: 10.1016/j.ijpharm.2014.06.026.
(73) Vandenheuvel, D.; Singh, A.; Vandersteegen, K.; Klumpp, J.; Lavigne, R.; Van Den Mooter, G. Feasibility of spray drying bacteriophages into respirable powders to combat pulmonary bacterial infections. *Eur. J. Pharm. Biopharm.* 2013, 84 (3), 578-582 DOI: 10.1016/j.ejpb.2012.12.022.
(74) Jain, N. K. & Roy, I. Effect of trehalose on protein structure. *Protein Sci.* 24-36 (2008). doi:10.1002/pro.3
(75) Tapia, H. & Koshland, D. E. Trehalose Is a Versatile and Long-Lived Chaperone for Desiccation Tolerance. *Curr. Biol.* 24, 2758-2766 (2014).
(76) Iyer, P. V. & Ananthanarayan, L. Enzyme stability and stabilization—Aqueous and non-aqueous environment. *Process Biochem.* 43, 1019-1032 (2008).
(77) Ohtake, S. & Wang, Y. J. Trehalose: Current use and future applications. *J. Pharm. Sci.* 100, 2020-2053 (2011).
(78) Vandenheuvel, D., Meeus, J., Lavigne, R. & Van Den Mooter, G. Instability of bacteriophages in spray-dried trehalose powders is caused by crystallization of the matrix. *Int. J. Pharm.* 472, 202-205 (2014).
(79) Vandenheuvel, D. et al. Feasibility of spray drying bacteriophages into respirable powders to combat pulmonary bacterial infections. *Eur. J. Pharm. Biopharm.* 84, 578-582 (2013).
(80) Kropinski, A. M.; Mazzocco, A.; Waddell, T. E.; Lingohr, E.; Johnson, R. P. Enumeration of Bacteriophages by Double Agar Overlay Plaque Assay; 2009; pp 69-76.
(81) Jahanshahi-Anbuhi, S. et al. Pullulan Encapsulation of Labile Biomolecules to Give Stable Bioassay Tablets. *Angew. Chemie Int. Ed.* 53, 6155-6158 (2014).
(82) Jahanshahi-Anbuhi, S. et al. Simple and ultrastable all-inclusive pullulan tablets for challenging bioassays. *Chem. Sci.* 7, 2342-2346 (2016).
(83) Leung, V. et al. Long-Term Preservation of Bacteriophage Antimicrobials Using Sugar Glasses. *ACS Biomater. Sci. Eng.* (2017). doi:10.1021/acsbiomaterials.7b00468

What is claimed is:

1. A polymer matrix comprising pullulan, trehalose, and one or more viruses, wherein the one or more viruses are incorporated within the polymer matrix and the polymer matrix preserves and/or stabilizes the one or more viruses, and wherein the matrix comprises about 10 wt % to about 50 wt % of pullulan and about 50 wt % to about 90 wt % of trehalose, based on the dry weight of the matrix.

2. The polymer matrix of claim 1 comprising about 30 wt % to about 45 wt % of pullulan and about 60 wt % to about 70 wt % of trehalose, based on the dry weight of the matrix.

3. The polymer matrix of claim 1, wherein the pullulan has a molecular weight in the range of about 100,000 Da to about 200,000 Da.

4. The polymer matrix of claim 1, wherein the polymer matrix is formed into a dried film or a shaped object.

5. The polymer matrix of claim 1, wherein the one or more viruses are preserved at a temperature of from about 2° C. to about 40° C.

6. The polymer matrix of claim 5, wherein the one or more viruses are preserved and/or stabilized for at least 3 months at the temperatures.

7. The polymer matrix of claim 1, wherein the one or more viruses are comprised in a vaccine.

8. The polymer matrix of claim 1, wherein the one or more viruses are selected from a live virus, an attenuated virus, an inactivated virus and a bacteriophage.

9. The polymer matrix of claim 8, wherein the one or more viruses are selected from a live virus, an inactivated virus and an attenuated virus.

10. The polymer matrix of claim 1, wherein the polymer matrix further comprises one or more additional substances or additives.

11. The polymer matrix of claim 10, wherein the additives change physical properties of the polymer matrix chosen from solubility, transparency, tactile impression, texture and plasticity.

12. The polymer matrix of claim 1, wherein the polymer matrix is amorphous.

13. The polymer matrix of claim 1, further comprising one of more biomolecules selected from a protein, an enzyme, an antibody, a peptide and a nucleic acid.

14. A polymer matrix comprising pullulan, trehalose and a virus, wherein the virus is incorporated within the polymer matrix and the polymer matrix preserves and/or stabilizes the virus, and wherein the matrix comprises about 10 wt % to about 50 wt % of pullulan and about 50 wt % to about 90 wt % of trehalose, based on the dry weight of the matrix.

15. The polymer matrix of claim 14, wherein the virus is a live virus, an attenuated virus, an inactivated virus or a bacteriophage.

16. A method of preserving and/or stabilizing one or more viruses comprising:

a. combining one or more viruses, pullulan, trehalose, and water to provide a mixture, and b. drying the mixture to form a polymer matrix which preserves and/or stabilizes the one or more viruses, wherein the matrix comprises about 10 wt % to about 50 wt % of pullulan and about 50 wt % to about 90 wt % of trehalose, based on the dry weight of the matrix.

17. The method of claim 14, wherein the trehalose is added to an aqueous solution of pullulan and the one or more viruses and the trehalose is added at a concentration of about 0.1 M to about 1 M.

18. The method of claim 16, wherein one or more additives are added to the mixture, to the one or more viruses, to the aqueous solution comprising pullulan and/or to the trehalose prior to drying.

19. The method of claim 16, wherein, the mixture is drop cast into a specific shape prior to drying.

20. The method of claim 16, wherein the mixture is formed into a film prior to drying.

21. The method of claim 16, wherein the polymer matrix comprises about 30 wt % to about 45 wt % of pullulan and about 60 wt % to about 70 wt % of trehalose, based on the dry weight of the matrix.

22. The method of claim 16, wherein the mixture is coated onto a substance or surface prior to drying.

23. The method of claim 16, wherein the trehalose is added to an aqueous solution of pullulan and the one or more viruses and the trehalose is added at a concentration of about 0.5 M.

* * * * *

UNITED STATES PATENT AND TRADEMARK OFFICE
CERTIFICATE OF CORRECTION

| | |
|---|---|
| PATENT NO. | : 11,040,015 B2 |
| APPLICATION NO. | : 16/161627 |
| DATED | : June 22, 2021 |
| INVENTOR(S) | : Vincent Ho Yin Leung et al. |

Page 1 of 1

It is certified that error appears in the above-identified patent and that said Letters Patent is hereby corrected as shown below:

In the Claims

Claim 17, Column 26, Line 4, "The method of claim 14" should read --The method of claim 16--.

Claim 18, Column 26, Line 10, "to the aqueous solution comprising pullulan" should read --to the pullulan--.

Signed and Sealed this
Fourth Day of April, 2023

Katherine Kelly Vidal
*Director of the United States Patent and Trademark Office*